US011141564B2

(12) United States Patent
Miraki et al.

(10) Patent No.: US 11,141,564 B2
(45) Date of Patent: Oct. 12, 2021

(54) SPRING CANNULAE

(71) Applicant: Edwards Lifesciences Corporation, Irvine, CA (US)

(72) Inventors: Manouchehr A. Miraki, Laguna Hills, CA (US); Bryan A. Janish, Huntington Beach, CA (US); Raymond J. McManus, Clearfield, UT (US); Brent K. Hoffman, Taylorsville, UT (US)

(73) Assignee: Edwards Lifesciences Corporation, Irvine, CA (US)

( * ) Notice: Subject to any disclaimer, the term of this patent is extended or adjusted under 35 U.S.C. 154(b) by 169 days.

(21) Appl. No.: 16/298,926

(22) Filed: Mar. 11, 2019

(65) Prior Publication Data

US 2019/0201661 A1    Jul. 4, 2019

Related U.S. Application Data

(63) Continuation of application No. 15/107,404, filed as application No. PCT/US2015/036005 on Jun. 16, 2015, now Pat. No. 10,226,595.

(Continued)

(51) Int. Cl.
*A61M 25/00* (2006.01)
*A61M 1/36* (2006.01)
*A61M 5/32* (2006.01)

(52) U.S. Cl.
CPC .......... *A61M 25/005* (2013.01); *A61M 5/329* (2013.01); *A61M 5/3291* (2013.01);
(Continued)

(58) Field of Classification Search
CPC ............ A61M 25/005; A61M 25/0052; A61M 25/0053; A61M 25/0051; A61M 25/007;
(Continued)

(56) References Cited

U.S. PATENT DOCUMENTS 4,351,341 A * 9/1982 Goldberg .......... A61B 17/22032
606/194
5,312,344 A    5/1994 Grinfeld et al.
(Continued)

FOREIGN PATENT DOCUMENTS

| EP | 0619745 A1 | 10/1994 |
| WO | 9964099 A1 | 12/1999 |
| WO | 2006093273 A1 | 9/2006 |

OTHER PUBLICATIONS

Int'l. Search Report for PCT/US2015/044003, dated Nov. 11, 2015.
Int'l. Search Report for PCT/US2015/036005, dated Sep. 21, 2015.

*Primary Examiner* — Nathan R Price
*Assistant Examiner* — Tasnim Mehjabin Ahmed
(74) *Attorney, Agent, or Firm* — Rick Cates

(57) ABSTRACT

Disclosed herein are embodiments of spring cannulae, including one or more holes in the sidewall of the cannula. Some disclosed cannulae include a wire, helically wound to form coils, and at least one hole in the cannula that interrupts one or more of the coils. Some embodiments further include a fused region of the coils through which the hole passes. Some embodiments include a ring attached to ends of the interrupted coils, where the hole is surrounded by the ring. Some embodiments include a sheath that is attached to a radial surface of the interrupted coils, where the hole passes radially though the sheath.

20 Claims, 22 Drawing Sheets

Related U.S. Application Data

(60) Provisional application No. 62/012,817, filed on Jun. 16, 2014.

(52) U.S. Cl.
 CPC ...... *A61M 25/007* (2013.01); *A61M 25/0012* (2013.01); *A61M 1/3659* (2014.02); *A61M 2205/0216* (2013.01); *A61M 2207/00* (2013.01)

(58) Field of Classification Search
 CPC ...... A61M 5/3291; A61M 2025/09058; A61M 25/09
 USPC .......................................................... 138/172
 See application file for complete search history.

(56) References Cited

U.S. PATENT DOCUMENTS

| | | |
|---|---|---|
| 6,099,506 A | 8/2000 | Macoviak et al. |
| 6,197,014 B1 | 3/2001 | Samson et al. |
| 6,533,770 B1* | 3/2003 | Lepulu .............. A61M 25/0012 |
| | | 604/264 |
| 6,626,872 B1 | 9/2003 | Navia et al. |
| 6,669,674 B1 | 12/2003 | Macoviak et al. |
| 2003/0004452 A1 | 1/2003 | Lenker |
| 2003/0176830 A1 | 9/2003 | Scheule |
| 2005/0192558 A1* | 9/2005 | Bernard .............. A61M 25/007 |
| | | 604/525 |
| 2005/0222532 A1 | 10/2005 | Bertolero et al. |
| 2009/0234291 A1 | 9/2009 | Saunders et al. |
| 2010/0241068 A1 | 9/2010 | Chen |
| 2011/0152741 A1 | 6/2011 | Banchieri et al. |
| 2012/0016408 A1 | 1/2012 | Barbut et al. |
| 2012/0259273 A1 | 10/2012 | Moshinsky et al. |
| 2012/0302953 A1 | 11/2012 | Don Michael |

\* cited by examiner

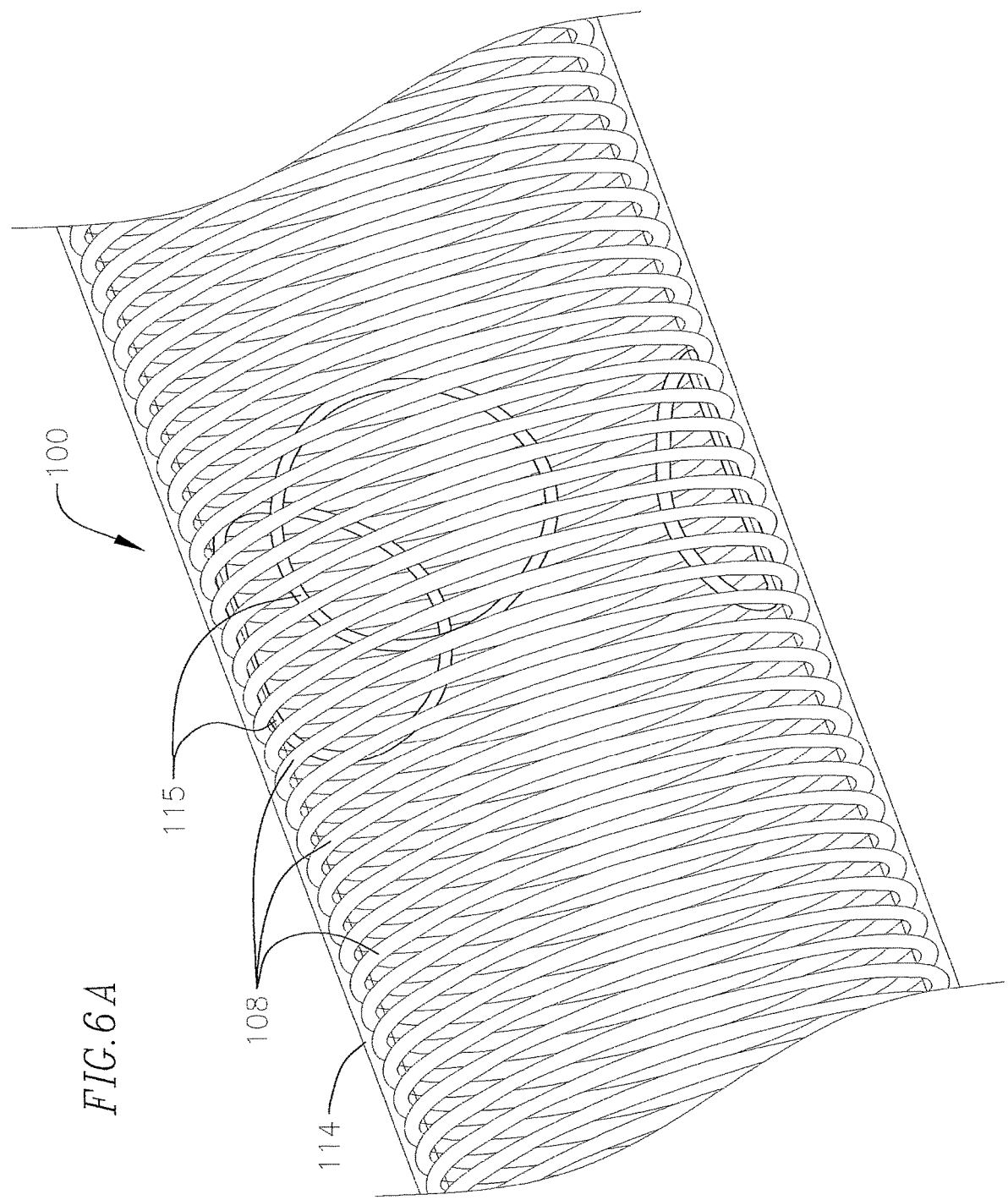

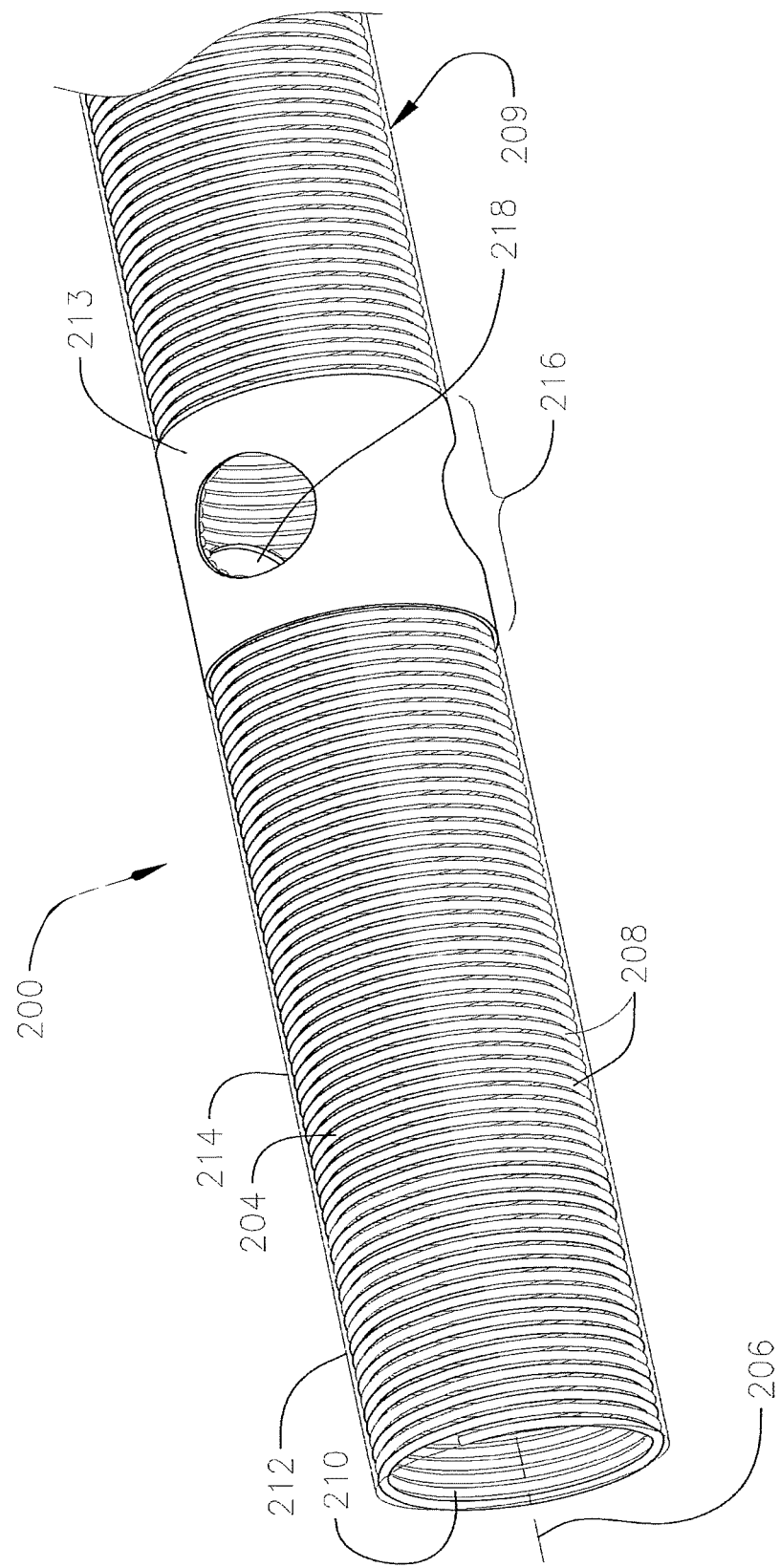

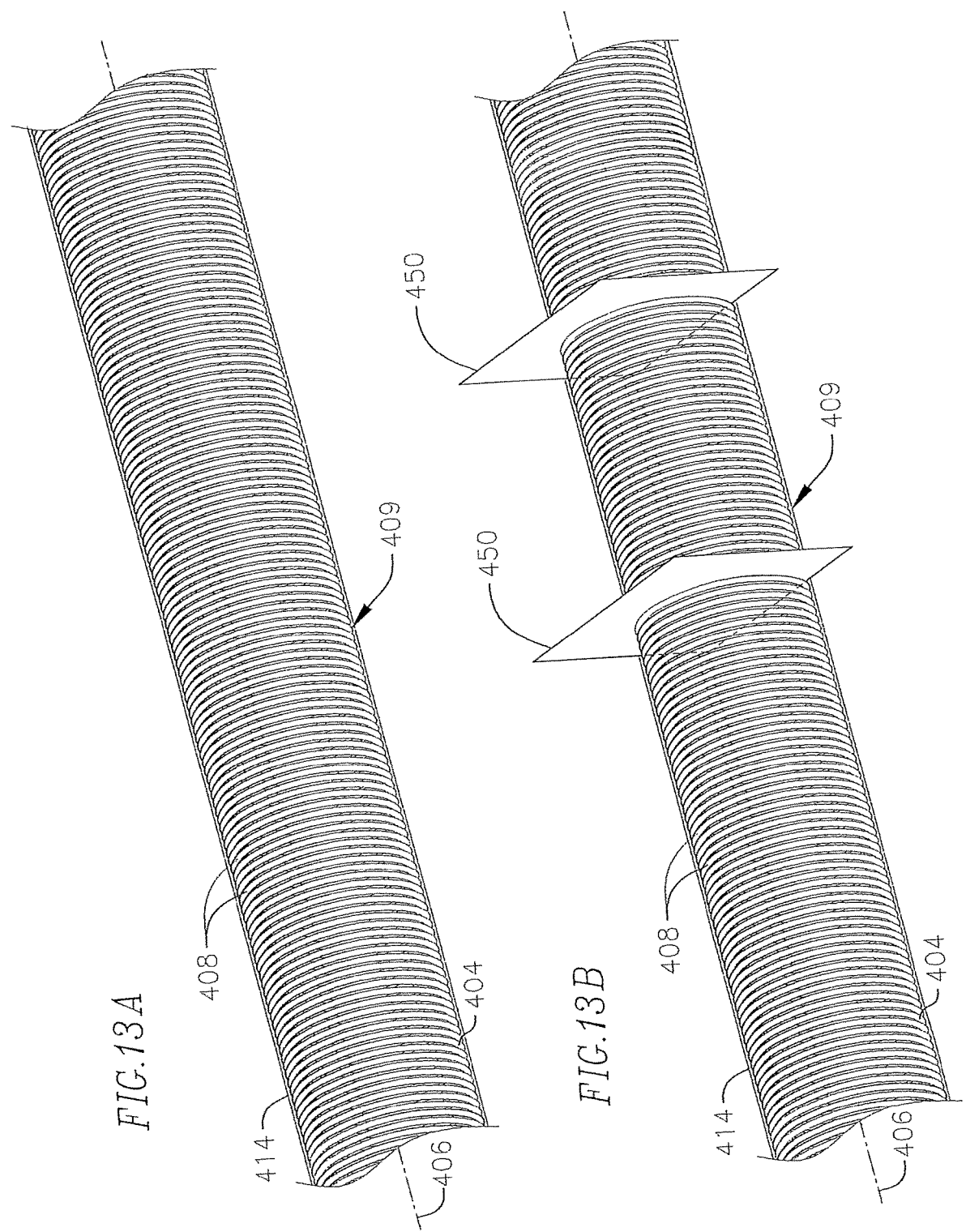

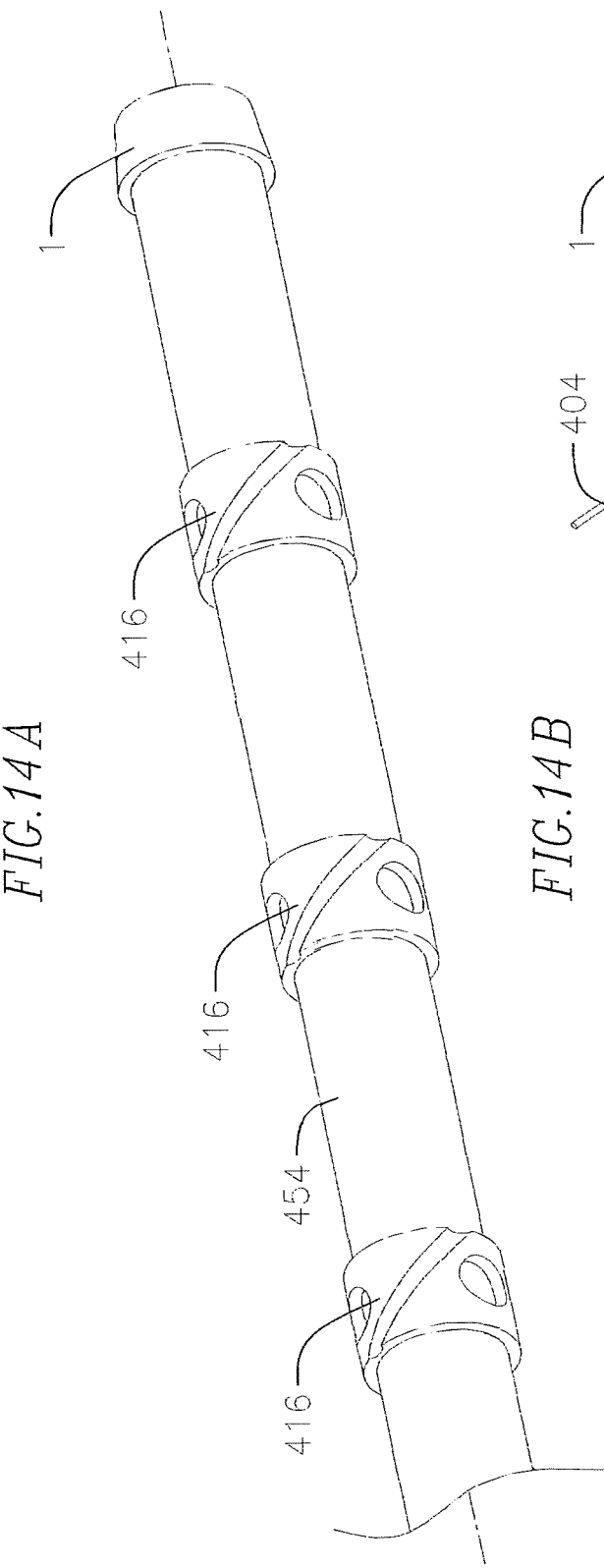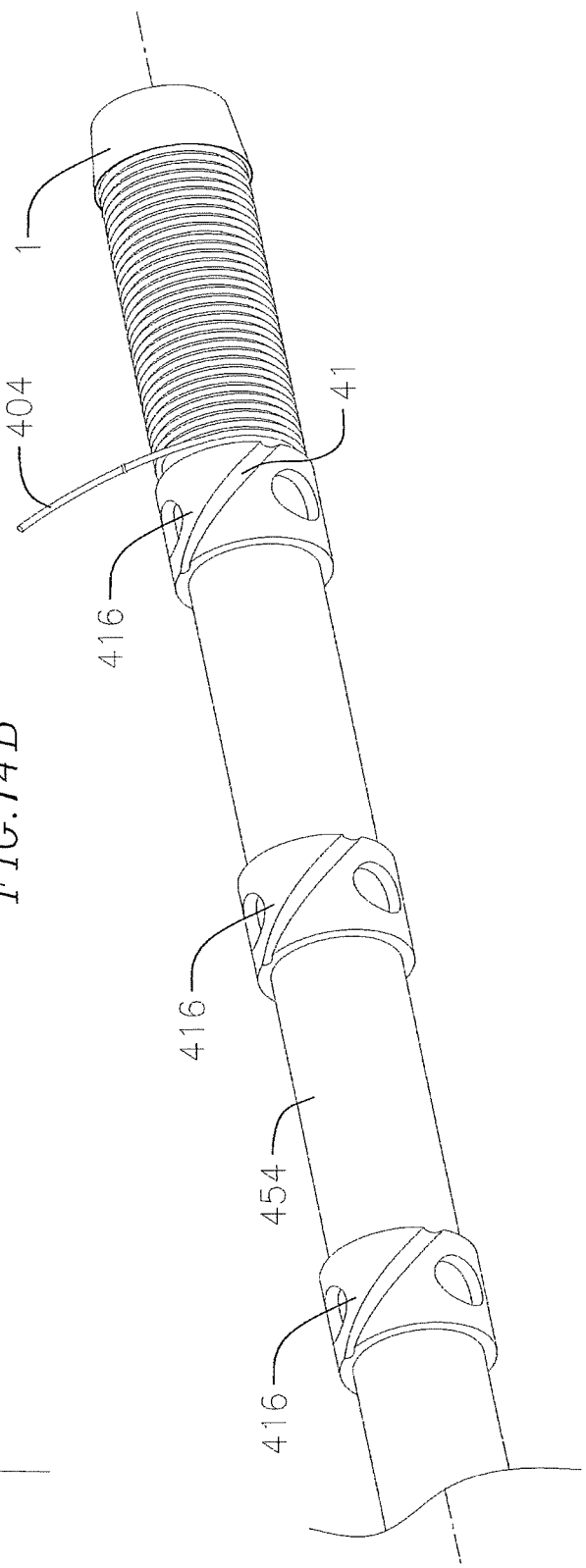

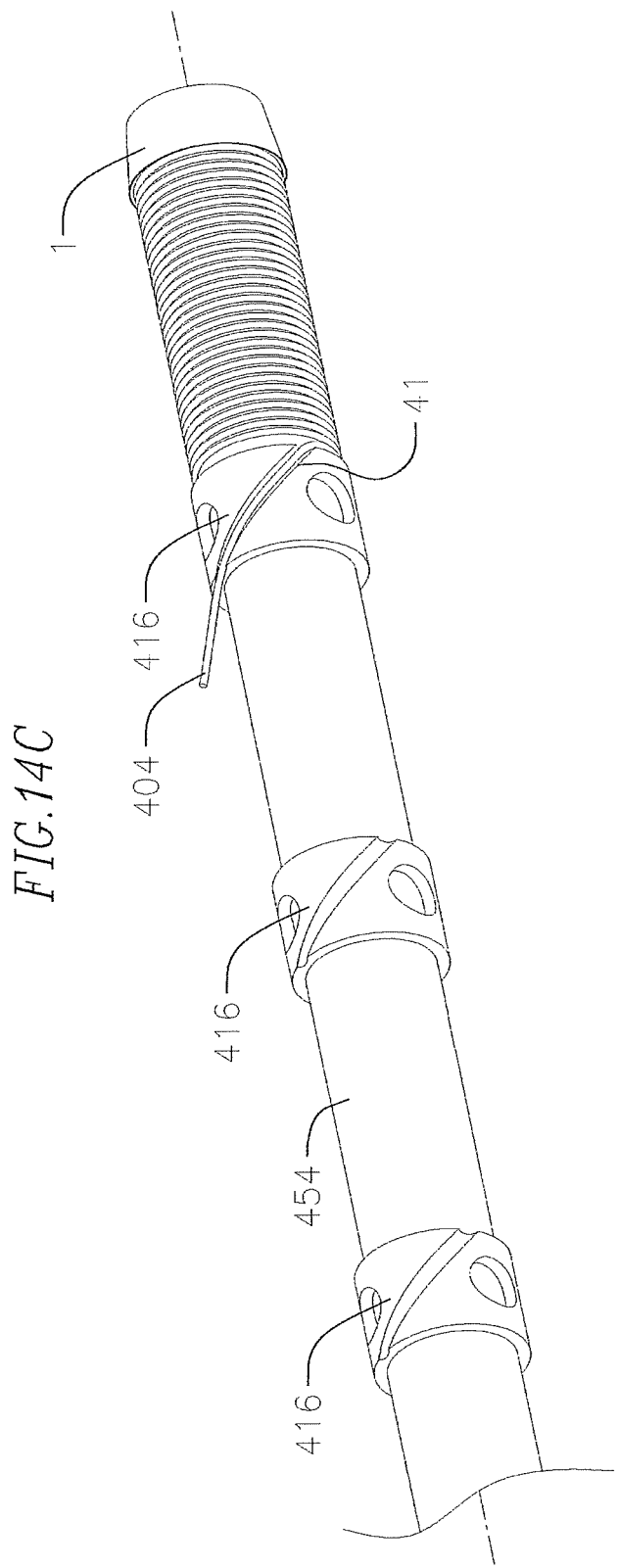

SPRING CANNULAE

CROSS REFERENCE TO RELATED APPLICATIONS

This application is a continuation of U.S. patent application Ser. No. 15/107,404, filed Jun. 16, 2015, now U.S. Pat. No. 10,226,595, which is the U.S. National Stage of International Application No. PCT/US2015/036005, filed Jun. 16, 2015, which claims the benefit of U.S. Patent Application No. 62/012,817, filed Jun. 16, 2014, the entire disclosures all of which are incorporated by reference.

FIELD

This disclosure relates to embodiments of spring cannulae having one or more holes in the sidewall to allow passage of a fluid through the sidewall, and to methods of manufacturing such spring cannulae. More specifically, spring cannulae according to embodiments of the invention can be used to draw blood from or to introduce blood to a patient during a surgical procedure where a cardiopulmonary bypass is utilized. For example, the spring cannulae can be positioned at or near a right atrium of the patient's heart to remove venous blood from the patient for oxygenation.

BACKGROUND

It is a routine requirement of a variety of surgical procedures to utilize extracorporeal cardiopulmonary bypass in order to mechanically perform the functions normally conducted by the heart and lungs. Venous blood depleted in oxygen and rich in carbon dioxide is removed from the patient and pumped to an oxygenating apparatus in order to oxygenate the blood and remove excess carbon dioxide. The blood is then returned to the patient's arterial system.

It is important that adequate volumes of blood be drained from the patient during cardiopulmonary bypass so that the extracorporeal life support equipment can keep up with the patient's need for oxygen and can adequately remove excess carbon dioxide. Insufficient quantities of oxygen can lead to serious tissue damage. Inadequate removal of carbon dioxide leads to a condition known as "acidosis," which can result in serious consequences caused by the alternation in normal metabolic functioning of critical enzymes. Either condition can result in serious injury to the patient.

A general technique involves using a drainage cannula to remove the venous blood from the patient for extracorporeal treatment. Such cannulae can have drainage openings at the distal end and also along their length proximal to the distal end. Such cannulae are inserted through the right atrium and extend into either the inferior vena cava or the superior vena cava or both, with the proximal drainage openings positioned within the right atrium. This placement permits blood to be drained simultaneously from the right atrium and from surrounding vena cavae.

Surgically placed cannulae are frequently used in various surgical procedures, such as, but not limited to the procedure described above, to draw blood from or introduce blood into patient vessels. In some cases there is a need for a cannula to have holes in the sidewall to allow blood flow through the sidewall during procedures. In cannulae, such as drainage cannulae, that have a sidewall made from a coiled spring, the holes along the length of the cannula can be formed by cutting the spring and placing a solid-walled tube between the two cut ends. Holes can then be punched into the solid-walled section of the cannula. However, this type of cannula design results in a weakness of the cannula in the area that has no spring, and the cannula can separate at the joints between the spring and solid-walled tube during use.

SUMMARY

Disclosed herein are embodiments of a spring cannula having one or more holes in the sidewall. The cannula includes at least one wire that is helically wound to form a plurality of coils defining a tubular sidewall of the cannula. The cannula further includes one or more holes passing radially through the sidewall, and in some embodiments, the holes interrupt one or more of the coils. The interrupted coils can be reinforced by being axially coupled to adjacent coils in a region surrounding the hole.

In some embodiments, the cannula includes a group of adjacent coils that are axially fused together, such as by welding, to form a fused region of the wire, and at least one hole passes radially through the fused region of the wire, such that the hole interrupts a plurality of the fused coils. The axial length of the hole can be less than an axial length of the fused region of the wire. The fused region includes one or more uninterrupted coils on either axial side of the hole that reinforces the interrupted coils.

In some embodiments, the cannula includes a ring surrounding the hole and connected to and reinforcing the interrupted coils. The ring can be attached to an inner or an outer surface of the coils, or the ring can be evenly positioned such that the ring and the coils are at about the same radial distance from a longitudinal center axis of the cannula. In some embodiments, a plurality of pieces of metal can be positioned (e.g., welded) in between the ends of the interrupted coils, and the ring can be formed from the ends of the interrupted coils together with the added pieces of metal.

In other embodiments, the cannula can include a reinforcing sheath attached to a radial surface of an adjacent group of the coils, where the adjacent group of coils includes the hole, the interrupted coils, and at least one un-interrupted coil at either axial side of the interrupted coils. The hole passes through the sheath and the coils. The sheath can be attached to an inner radial surface or an outer radial surface of the coils. The sheath can be a solid metal tube welded to the coils, for example, or the sheath can include an inner layer comprising metal, and an outer layer comprising a polymer that shrinks over the sheath and coils.

In any of the above embodiments, the cannula can further include a polymeric coating that encases the coils but does not block the hole(s).

In alternative embodiments, a cannula can include a wire that is helically wound to form a tubular spring comprising a plurality of coils that define a sidewall of the cannula and are not interrupted by the sidewall hole(s). The plurality of coils can include one or more coils that are elongated in an axial dimension relative to adjacent coils to provide space therebetween for the hole(s).

In alternative embodiments, a cannula includes a wire and an insert. The wire is helically wound to form a plurality of coils, wherein the plurality of coils includes at least one coil portion that is wound at a smaller angle relative to a central axis of the cannula than adjacent coils positioned at opposite ends of the at least one coil portion, such that the at least one coil portion is stretched axially relative to the adjacent coils. The insert includes a porous section defining at least one hole passing radially through the insert, wherein the insert is positionable between the adjacent coils and the at least one coil portion is positionable on the insert and is spaced apart from the at least one hole.

In some embodiments, a method of manufacturing the above cannula includes winding the wire to form the plurality of coils and the at least one coil portion, positioning the insert corresponding to the at least one coil portion between the adjacent coils heating a region around the insert to bond the insert with the wire; and heating the entire cannula to seal gaps between adjacent ones of the plurality of coils.

The foregoing and other objects, features, and advantages of the disclosed technology will become more apparent from the following detailed description, which proceeds with reference to the accompanying figures.

BRIEF DESCRIPTION OF THE DRAWINGS

FIG. 6A-6B are perspective views of a portion of the wire body shown in FIG. 5, illustrating the position of the rings on the coils before and after sidewall holes are made within the rings.

FIG. 7 is a perspective view of a portion of a wire body of another alternative spring cannula in which the porous region is covered in a sheath overlaying coils of the wire body, where the wire body is encased in a coating which is partially cut away to show the coils.

FIGS. 13A-13D show a method of making the spring cannula of FIG. 11.

FIGS. 14A-14D show an alternative method of making the spring cannula of FIG. 11.

DETAILED DESCRIPTION

The present disclosure provides improved cannula designs, particularly for spring cannulae that have a wire body (such as a helically coiled wire body or spring) with at least one porous region having one or more holes in sidewalls of the porous region. Previous cannula designs included a solid-walled section inserted between two cut ends of a coiled spring, with sidewall holes being formed in the solid-walled section. However, this design has points of weakness at the joints where the ends of the spring are attached to the ends of the solid-walled section, which can result in kinks or breakages of the cannula at those points during use. The embodiments disclosed herein offer a stronger and more reliable solution to cannula design to reduce or prevent cannula breakage. Some disclosed embodiments include a hole that cuts through the coils of the spring. However, these embodiments include reinforcement of the cut spring coils proximal to the hole, such that the interrupted coils, those coils that have been cut to make the hole, are supported and reinforced to prevent breakage or the formation of kinks adjacent to the hole. Some embodiments include transition sections having holes that are inserted between the coils of the wire body without cutting the coils adjacent to the transition sections such that the coils of the wire body are continuous through the transition sections. The continuous coil design allows the catheter to be more easily retrievable than prior cut designs where there was a risk of breakage at the cut points. The continuous coil design also reduces the potential for exposure to cut edges at the coil ends.

Figure 1:
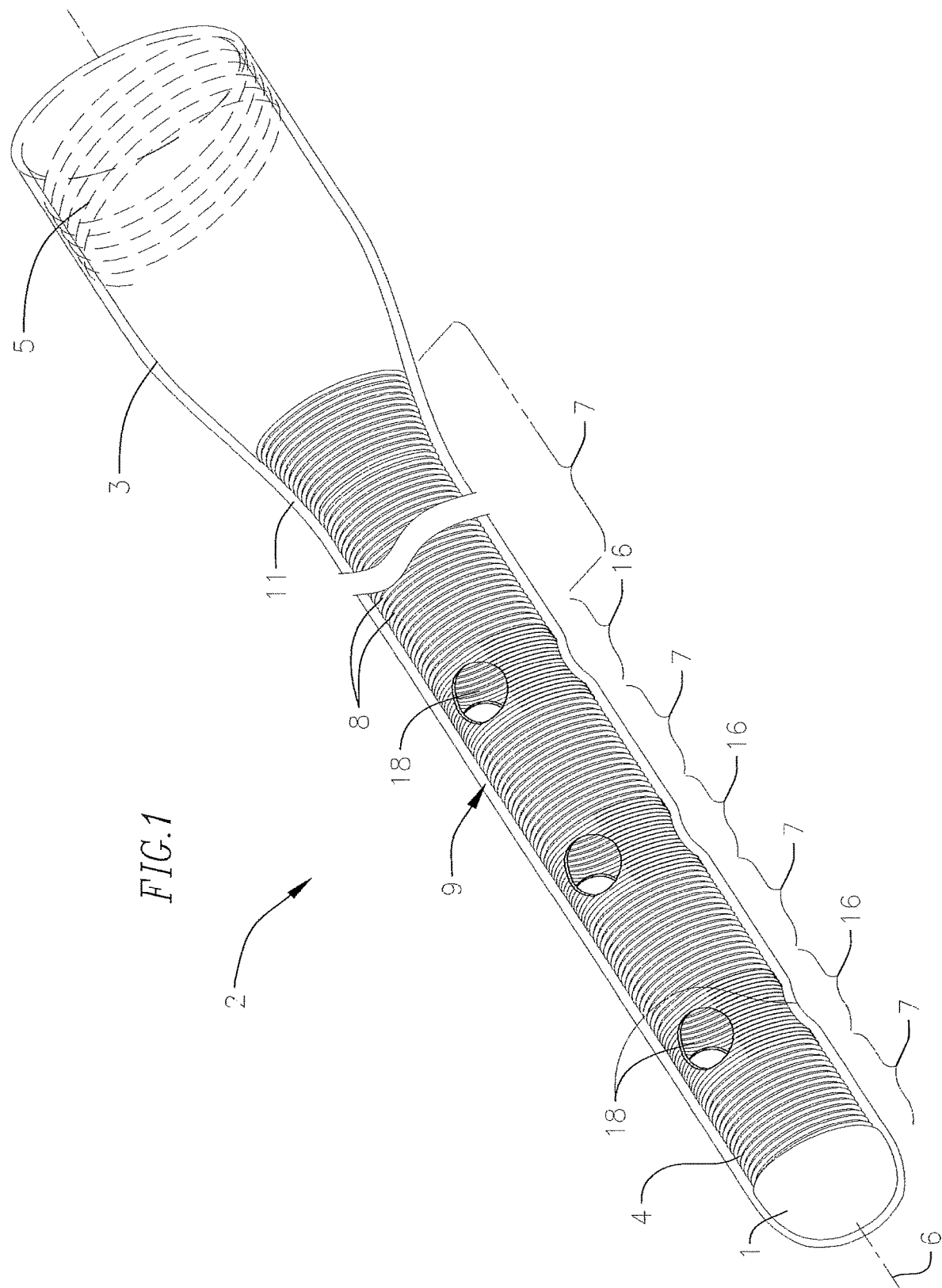
FIG. 1 is a perspective view of a spring cannula having a wire body with porous regions according to a first embodiment.

FIG. 1 shows a spring cannula 2 having a wire body 9 with porous regions 16.

The spring cannula 2 is made of a continuous helically coiled wire 4 that extends from a distal end having a tip 1 to a proximal end having a connector 3. The wire 4 can be a flat wire and can have a diameter of 0.008 inches. The portion of the spring cannula 2 that includes the wire 4 is referred to as the wire body 9. The spring cannula 2 can be formed from at least one wire 4, helically wound around a central axis 6 to form a plurality of coils 8. The tip 1 is flexible and can have a smaller diameter than the wire body 9 to facilitate insertion and/or advancement of the tip 1, for example, through a patient's body and into the heart or a superior or inferior vena cava of the patient during surgery. The tip 1 can also include holes to allow blood flow through the tip 1 during medical procedures. For example, the tip 1 can include drainage holes to collect blood from the vena cava during surgery, such as during cardiopulmonary bypass surgery.

The connector 3 has threads 5 to correspond to threads of tubing or additional devices for use with the cannula 2 during surgery. For example, the threads 5 can correspond to threads on an intake tube of a cardiopulmonary bypass machine. In such an embodiment, when the spring cannula 2 is connected to the cardiopulmonary bypass machine and the machine is in use, blood is collected by the spring cannula 2 and circulated through the bypass machine to remove carbon dioxide and to oxygenate the blood prior to the blood being returned to the body. Any other connection means suitable for such a connection can also be used in other embodiments.

In FIG. 1, the wire body 9 includes three porous regions 16 flanked by four wire reinforced regions 7. However, the number of porous regions 16 and wire reinforced regions 7 can vary in other embodiments. For example, in some embodiments, there are only two porous regions and three wire reinforced regions surrounding the porous regions. In other embodiments, there is only one porous region. In other embodiments, there can be more than three porous regions. In addition, the porous regions need not be flanked by wire reinforced regions. For example, the porous region closest to the tip of the spring cannula can be directly adjacent to the tip without a wire reinforced region therebetween.

Each porous region 16 includes one or more holes 18. In the illustrated embodiment, in each of the porous regions 16, three holes 18 are evenly spaced circumferentially and the holes 18 are axially aligned. However, the number of holes 18 in a porous region 16 can vary depending on the application, and in some embodiments the holes 18 are not axially aligned. For example, two or more holes can be adjacent or aligned along the central axis 6 of the spring cannula 2. In some embodiments, the organization of the holes in each of the porous regions can vary from one another. In addition, the holes can vary in size and shape.

Figure 3:
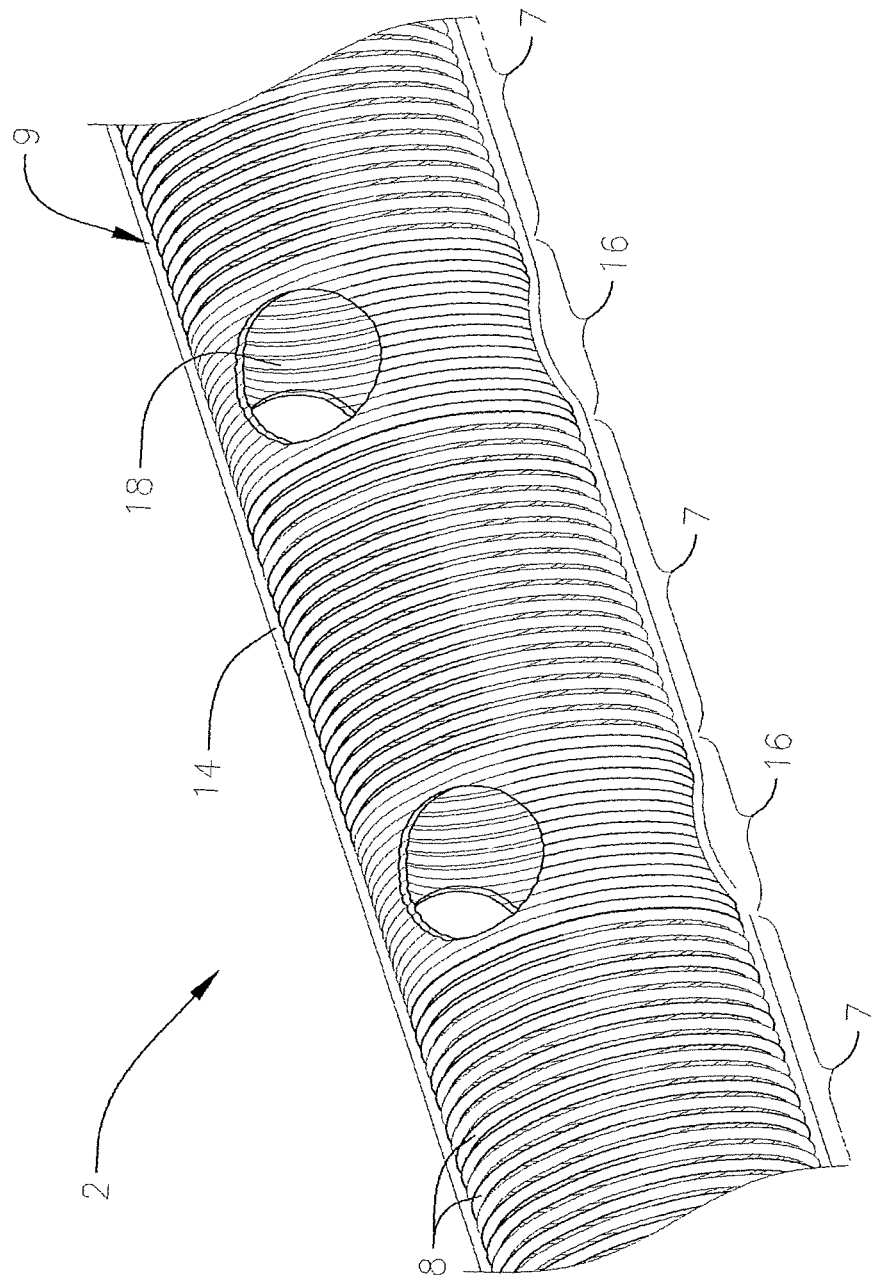
FIG. 3 is a perspective view of a portion of a wire body of a spring cannula according to an embodiment in which a porous region comprises a fused region.

The spring cannula 2 also has an overcoat 11. The overcoat 11 can be made of a thermoplastic polyurethane elastomer (TPU). For example, the overcoat 11 can be made of Tecothane™. The overcoat 11 can cover the entire spring cannula 2, including the tip 1, the wire body 9 and the connector 3, thereby integrating the tip 1, the wire body 9 and the connector into one continuous cannula, or it can cover portions of the cannula 2, such as the tip 1 and the wire body 9, but not the connector 3. However, in some embodiment, the overcoat 11 may not be needed and can be omitted. In some of the following illustrative embodiments, the overcoat 11 has been omitted to facilitate depiction of the underlying structures. In some embodiments, the wire 4 that forms the spring coils 8 has an additional coating 14, as shown in FIG. 3. The coating 14 can be a polymeric material, for example, a thermoplastic polyurethane elastomer such as Pellethane®, that is coated on the wire 4 before the wire 4 is wound to form the wire body 9. After winding, the coated wire can be heat-treated such that the polymeric coating on each coil bonds or fuses with the coating on the adjacent coils and forms the substantially continuous, flexible coating 14 that encases the coils 8. The coating 14 can be used in addition to, or alternative to, the overcoat 11.

In any of the embodiments disclosed herein, the wire 4 can be made from any suitable material, such as stainless steel (such as 304V stainless steel wire), nitinol, or other biocompatible metals. Some embodiments can comprise two or more discrete wires that are helically wound together. The plural wires can be wound in parallel with each other, such as with two wires forming a double helix, or the wires can be wound in opposing directions. The additional wire(s) can provide advantages compared to single-wire embodiments, such as providing better torque for the cannula, improving the strength of the cannula while still maintaining flexibility, and providing redundancy in the event that one wire should fail.

Figure 2:
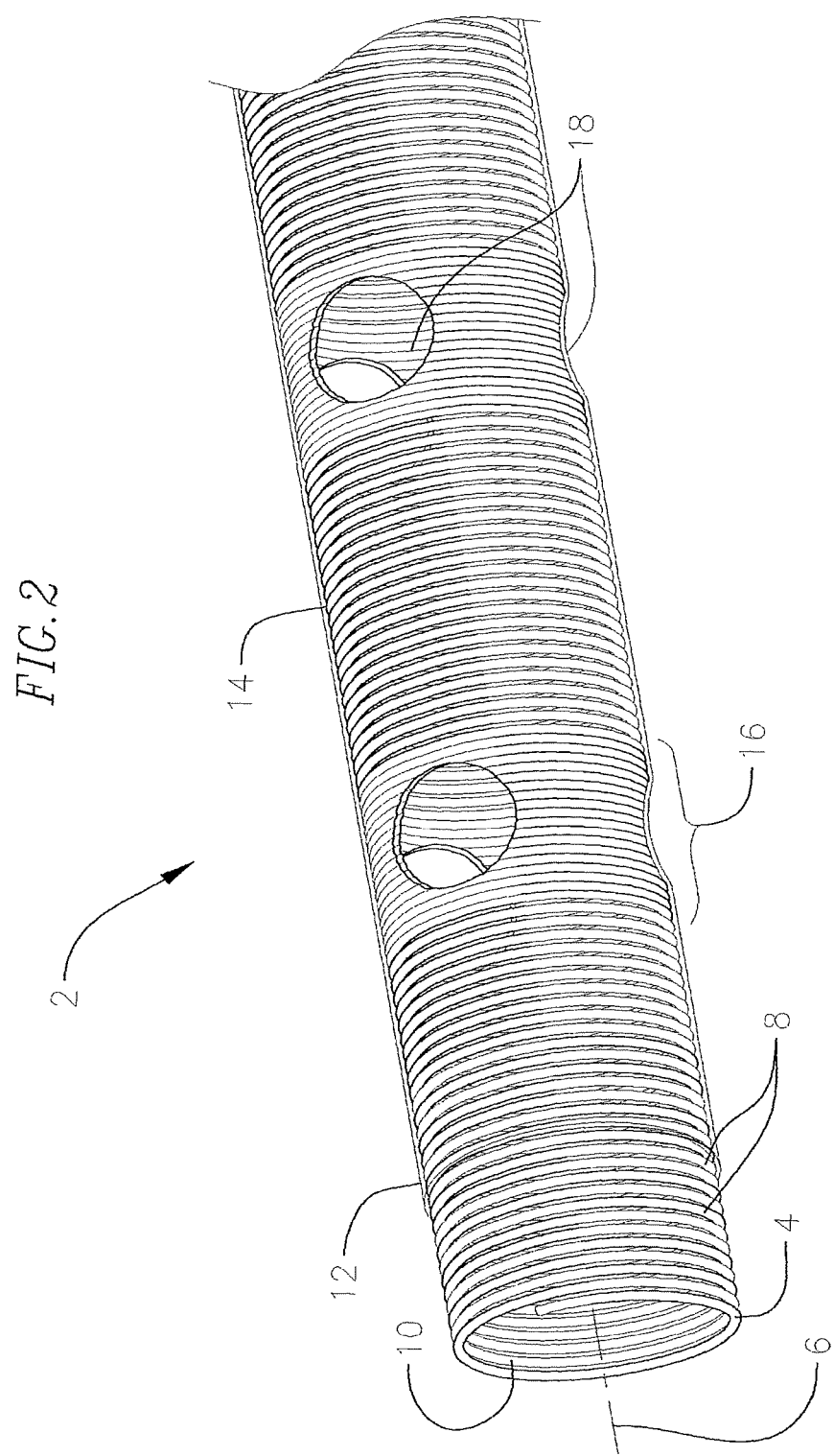
FIG. 2 is a perspective view of a portion of the wire body of the spring cannula of FIG. 1 where a coating is partially cut away to show coils of the wire body.

FIG. 2 shows a portion of the wire body 9 of the spring cannula 2 of FIG. 1 where the coating 14 is partially cut away to more clearly show the coils 8 of the wire body 9.

The coils 8 collectively define a radially inner surface 10 and a radially outer surface 12 of the cannula 2. The coils 8 provide flexibility and strength to the spring cannula 2, helping to prevent kinking and breakage while allowing for flexible movement during surgery.

As discussed above, the wire 4 can comprise stainless steel, for example. In some embodiments, the wire 4 is coated with a polymeric coating that is applied to the wire 4 before it is wound to form the coils 8. After the coils 8 are wound, the wire 4 can be heat-treated such that the polymeric coating melts to form the continuous coating 14 (partially cut away at front left of FIG. 1 to show the coils) that encases the coils 8, and forms the wire body 9 of the cannula 2.

FIG. 3 shows a portion of a wire body 9 of a spring cannula 2 in which at least one of the porous regions 16 comprises a fused region.

Figure 4:
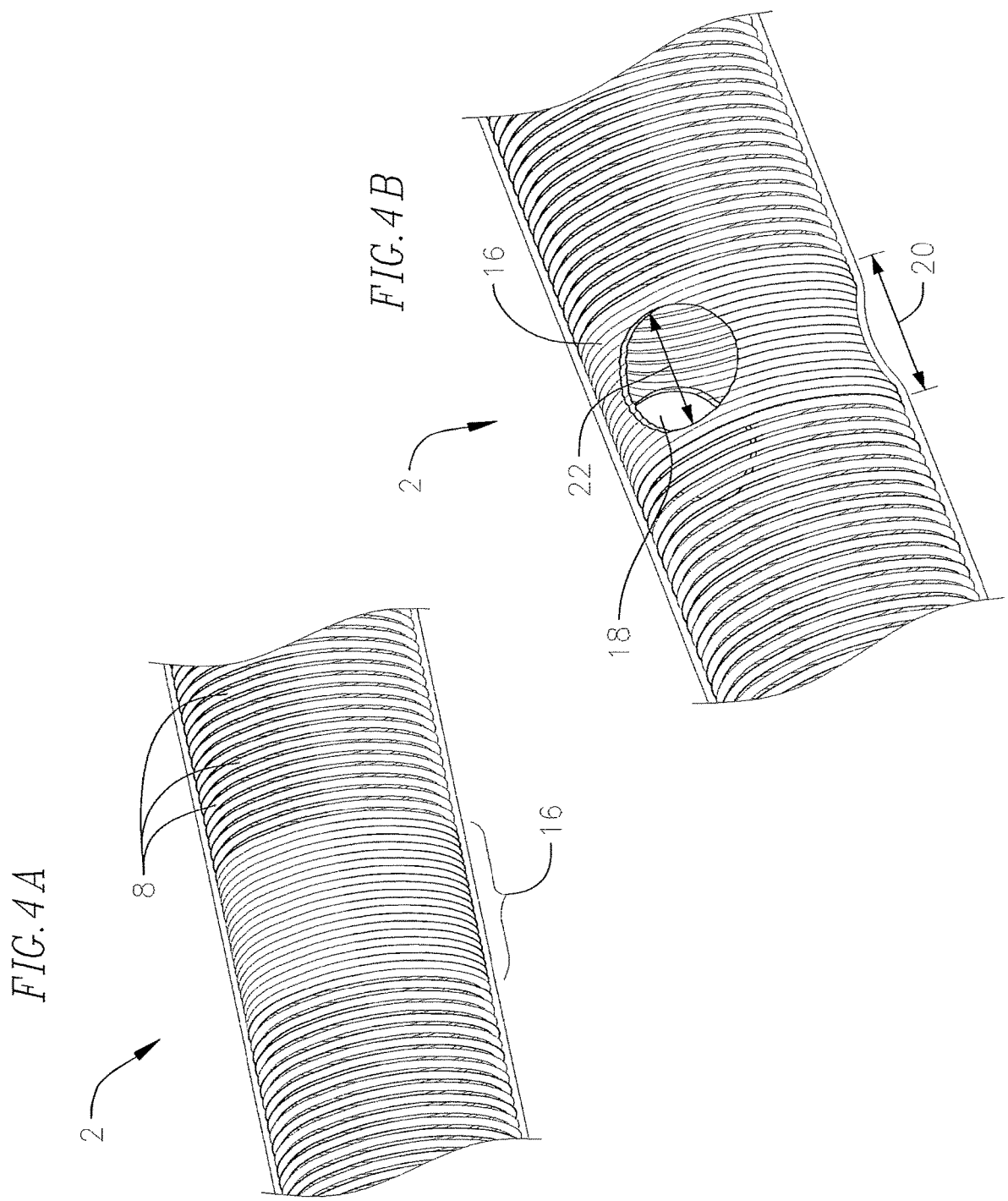
FIGS. 4A-4B are perspective views of a portion of the wire body shown in FIG. 3, illustrating the fused region prior to and after forming sidewall holes in the fused region.

In this embodiment, the spring cannula 2 includes the fused region 16, formed by fusing a plurality of coils 8 together (see, e.g., FIG. 4A). The coils 8 are compressed together in the fused region 16 so that the sides of each adjacent coil touch and/or are fused together, forming a relatively more rigid tubular section. The fused region 16 can be formed by removing the polymeric coating 14 from the area of the coils to be fused, and welding the exposed areas of the coils together. The coils can alternatively be fused together in other ways such as by bonding with an adhesive. One or more holes 18 (three in the illustrated embodiment of FIG. 4B) can be formed in the fused region 16 (partially or entirely in the fused region), by cutting through and interrupting a plurality of the fused coils. Even though several coils 8 are cut and interrupted in the fused region 16, the region maintains structural integrity because some of the fused coils (e.g., the coils at the axial ends of the fused region) are not interrupted and reinforce the interrupted coils. The polymeric coating 14 can optionally be re-formed over the fused region 16, but not over the holes 18. The holes 18 can be formed by any suitable means, such as punching, or cutting, for example by a laser. The fused region 16 is formed from sufficient coils 8 to have an axial length 20 that is greater than an axial length 22 of the holes 18 (FIG. 4B). In the illustrated embodiment, the three holes 18 are evenly spaced circumferentially and are axially aligned. However, the number of holes in a fused region can vary depending on the application, and in some embodiments the holes are not axially aligned. Additionally, a cannula can have multiple fused regions 16 as shown in FIG. 3, each with one or more holes 18.

Figure 5:
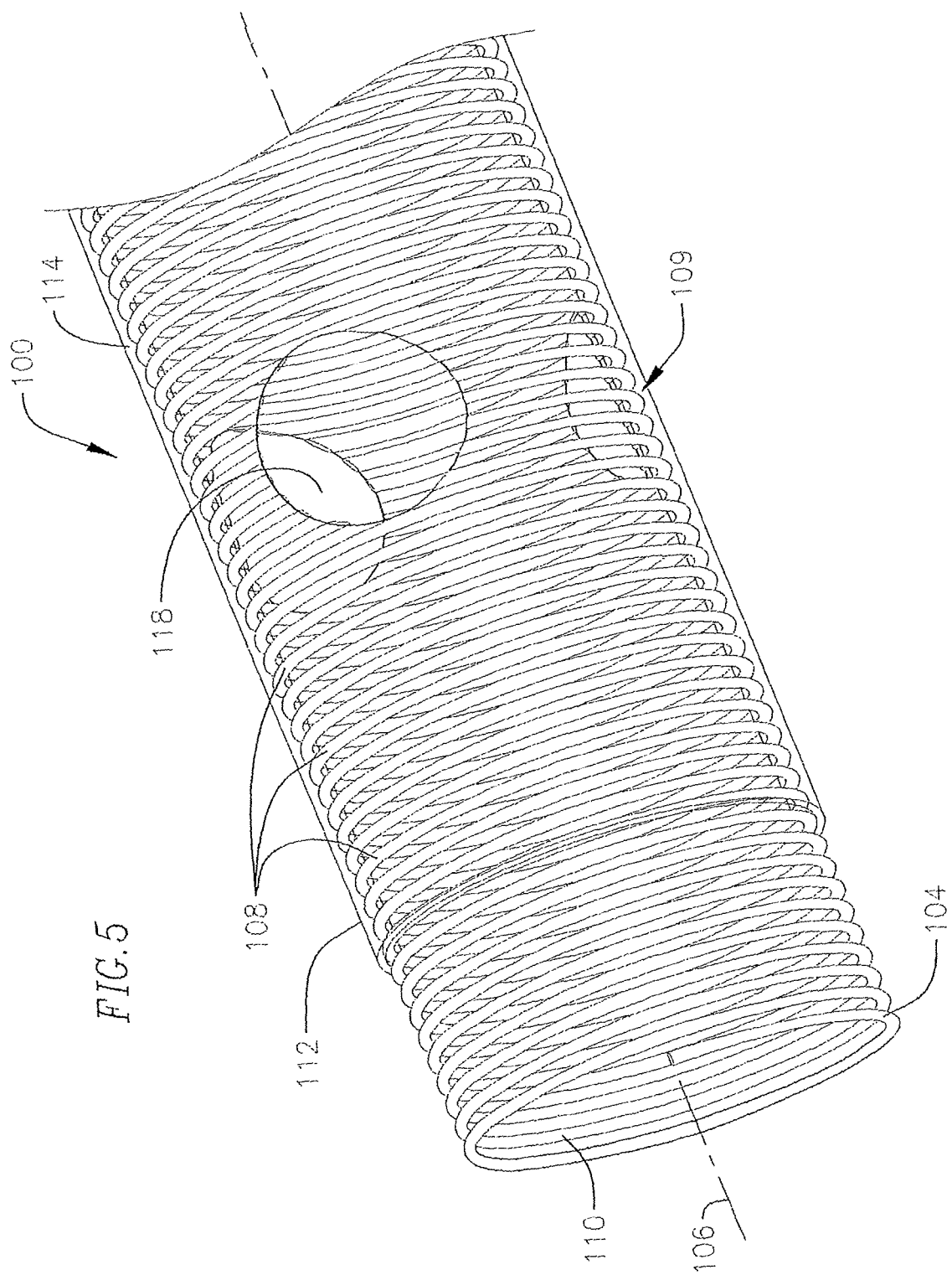
FIG. 5 is a perspective view of a portion of a wire body of an alternative spring cannula in which a porous region comprises rings and where the wire body is encased in a coating which is partially cut away to show coils of the wire body.
Figure 6B:
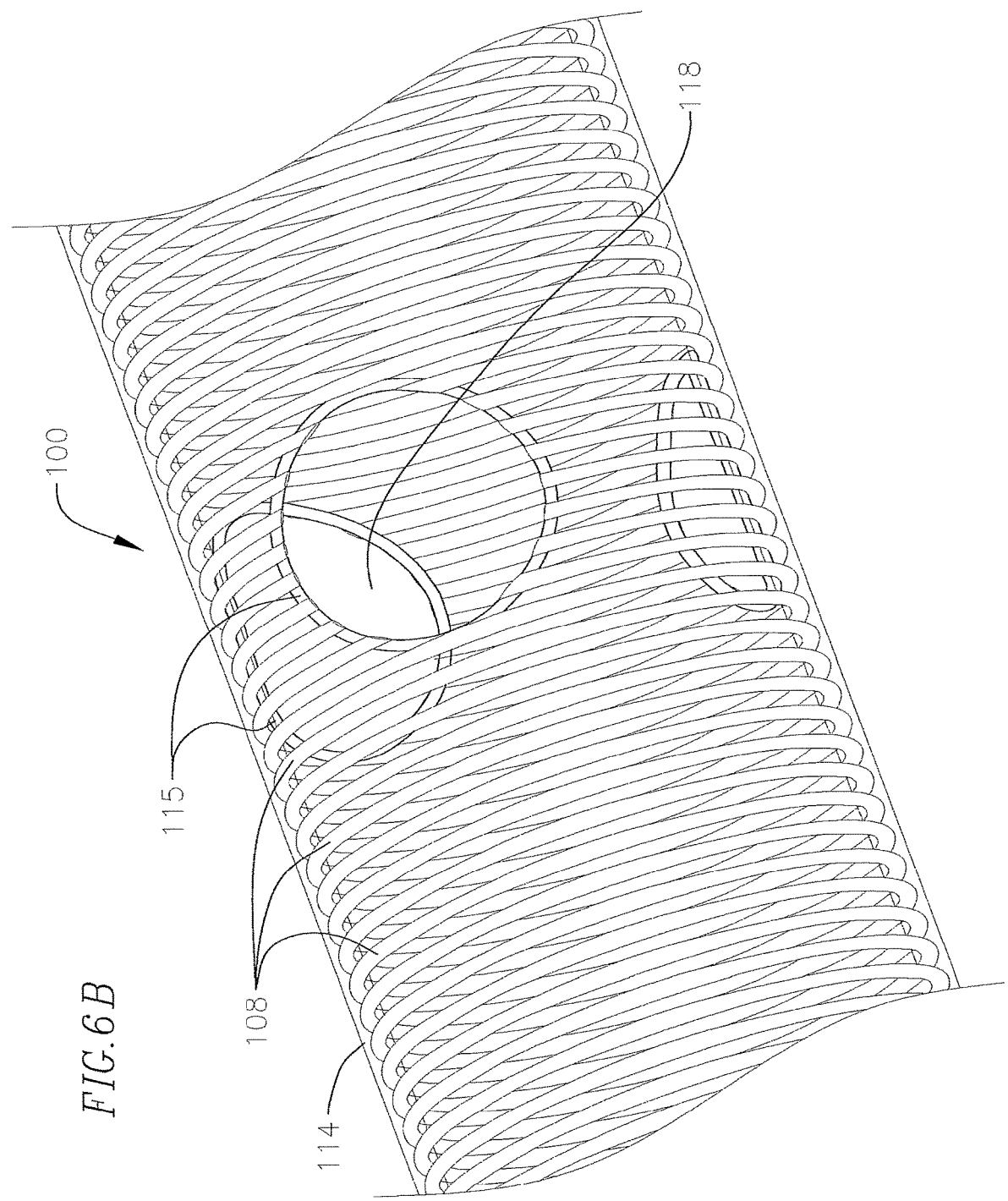

FIGS. 5 to 6B show a portion of a wire body 109 of an alternative spring cannula 100 in which a porous region 116 comprises rings 115 and where the wire body 109 is encased in a coating 114, which is partially cut away in FIG. 5 to more clearly show coils 108 of the wire body 109.

The alternative spring cannula 100 is shown having holes 118 in its sidewall. The cannula 100 can be formed from one or more wires 104, helically wound around a central axis 106 to form a plurality of coils 108. In some embodiments, the wire 104 is a stainless steel wire. In some embodiments, the wire 104 is coated with a polymeric coating, applied to the wire before it is wound to form the coils 108. The coils 108 collectively define a radially inner surface 110 and a radially outer surface 112 of the cannula 100. After the coils are wound, the wire can be heat-treated such that the polymeric coating melts to form a coating 114 (partially cut away in front to show the coils) that encases the coils 108, and forms the cannula 100.

One or more rings 115 can be attached to, or formed between, the coils 106, as shown in FIG. 6A, in order to reinforce the holes 118. The polymeric coating 114 can be removed from the portion of the coils 108 that are attached to the rings 115. In some embodiments, the rings 115 can be attached to either the inner surface 110 or the outer surface 112 of a group of adjacent coils 108. In such embodiments, each ring 115 can be attached, such as by welding, to each coil 108 in the group of adjacent coils at each point of contact between the ring 115 and each coil 108.

As shown in FIG. 6B, the holes 118 can be formed within the rings 115 and pass radially through the coils 108, such that each hole interrupts the group of adjacent coils attached to the respective ring. Each hole 118 is enclosed within a ring 115, such that the inner dimensions of the ring correspond to the dimensions of the hole, and the ring 115 is attached to the ends of the coils 108 that are interrupted by the hole.

In some embodiments, one or more rings 115 can be placed or formed even with the coils 108 such that a radial distance from the central axis 106 to the inner side of the ring is substantially the same as a radial distance from the central axis 106 to the inner surface 110 of the coils. In some embodiments, pieces of metal are placed in between and attached to (e.g., by welding) the ends of the interrupted coils, such that the pieces of metal together with the ends of the interrupted coils form the ring 115. In other embodiments, a hole can be cut that interrupts the coils and then a fully annular ring can be placed within the hole, such that the ends of the interrupted coils are in contact with the perimeter of the annular ring. The ring can be attached to the ends of the interrupted coils by welding or otherwise.

The rings 115 can be formed from the same material as the wire 104, or from a different material. There can be one or more rings 115 attached to the wire 104. In the illustrated embodiment there are three rings 115 (FIG. 6A). The polymeric coating 114 can optionally be reformed over the cut coils and the ring, but not over the holes 118.

FIG. 7 shows a portion of a wire body 209 of another alternative spring cannula 200 in which the porous region 216 is covered in a sheath 213 overlaying coils 208 of the wire body 209.

The spring cannula 200 is shown having holes 218 in its sidewall. The cannula 200 can be formed from one or more wires 204 wound helically about a central axis 206 to form a plurality of coils 208. In some embodiments, the wire 204 comprises stainless steel. In some embodiments, the wire is coated with a polymeric coating, applied to the wire before it is wound to form the coils 208. The coils 208 collectively define a radially inner surface 210 and a radially outer surface 212 of the cannula 200. After the coils are wound, the wire can be heat-treated such that the polymeric coating melts to form a coating 214 (partially cut away in FIG. 7 to show the coils) that encases the coils 208, and forms the cannula 200.

As shown in FIG. 7, the cannula 200 includes a sheath 213 connected to the outer surface 212 of a group of adjacent coils 208. In an alternative embodiment, the sheath 213 is connected to the inner surface 210 of the coils 208. A portion of the coating 214 can be removed to allow connection between the sheath 213 and the wire 204. The sheath 213 can be made from the same material as the wire 204, such as from stainless steel, or it can be made from a different material. In some embodiments, the sheath 213 is welded to the wire 204, such as by laser welding. In other embodiments, an adhesive is used to attach the sheath 213 to the wire 204.

In some embodiments, the sheath 213 comprises at least one additional layer, such as in a dual layer sheath, including a polymeric layer. Such a sheath 13 can include an inner metal layer and an outer polymeric layer, and can be attached to the wire 204 by a heat treatment, for example, by heat shrinking the polymeric layer over the metal later and some of the coils 208.

Figure 8:
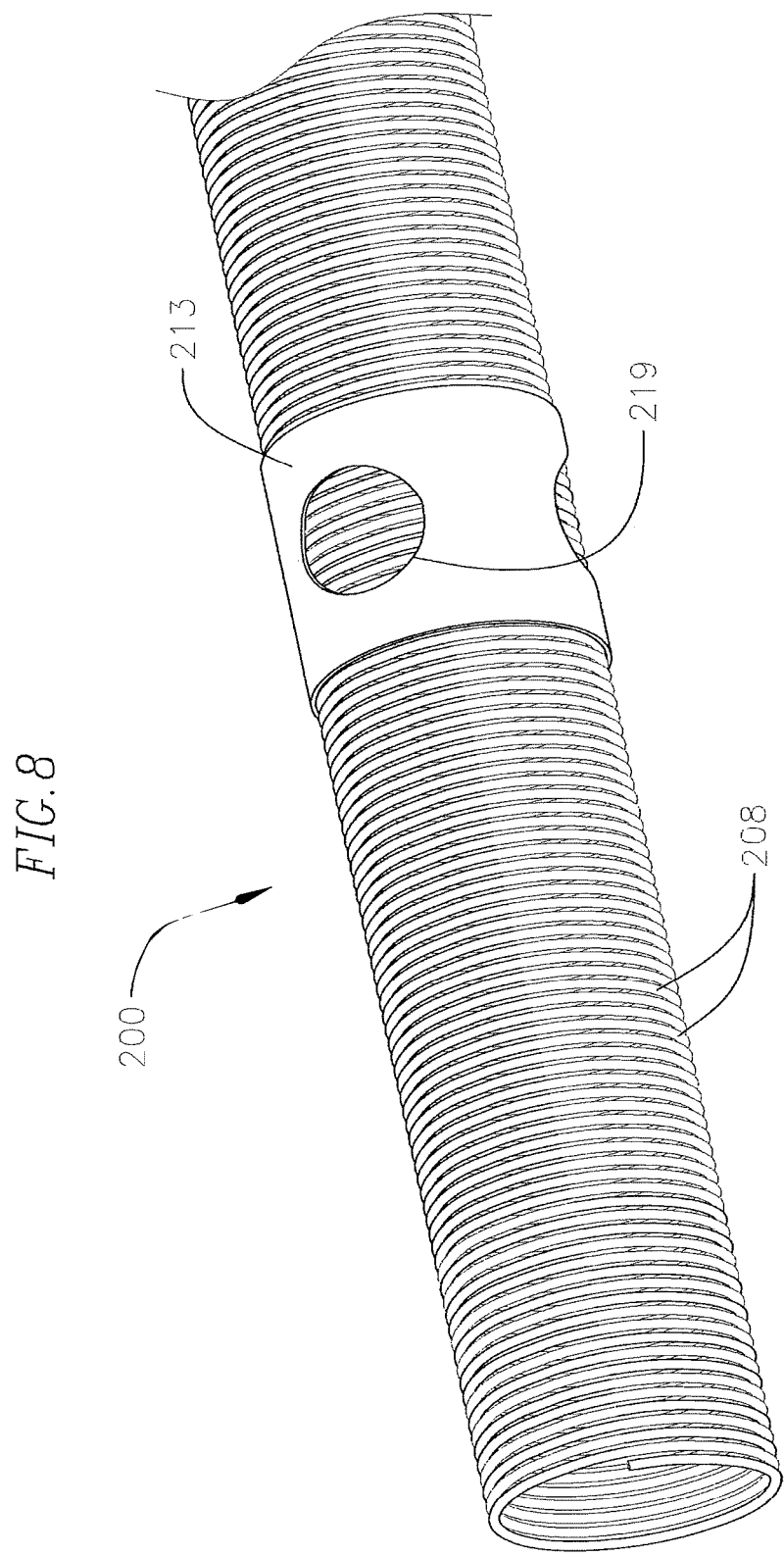
FIG. 8 is a perspective view of the coils and sheath of the cannula of FIG. 7 before sidewall holes are formed through the coils.

One or more holes 218 pass radially through both the sheath 213 and the group of adjacent coils 208 that are in contact with the sheath, such that the hole interrupts a portion of the coils. In some embodiments, pre-formed holes 219 can be made in the sheath 213 before the sheath is placed on the coils 208 (FIG. 8), and then the holes 218 are cut through the coils 208, such as by a laser, after the sheath 213 is attached to the cannula 200, using the pre-formed holes 219 in the sheath as a guide. In an alternative embodiment, a sheath 213 without pre-formed holes is attached to the coils 208, and the holes 218 are then made through both the coils 208 and sheath 213 at the same time.

In some embodiments, the sheath has an outer diameter less than or about the same as an outer diameter of the polymeric coating. In such embodiments, after the sheath has been attached to the coils, the maximum outer diameter of the cannula in the region of the holes is not increased.

In some embodiments, the polymeric coating can be reformed over the sheath, while not obstructing the holes.

Figure 9:
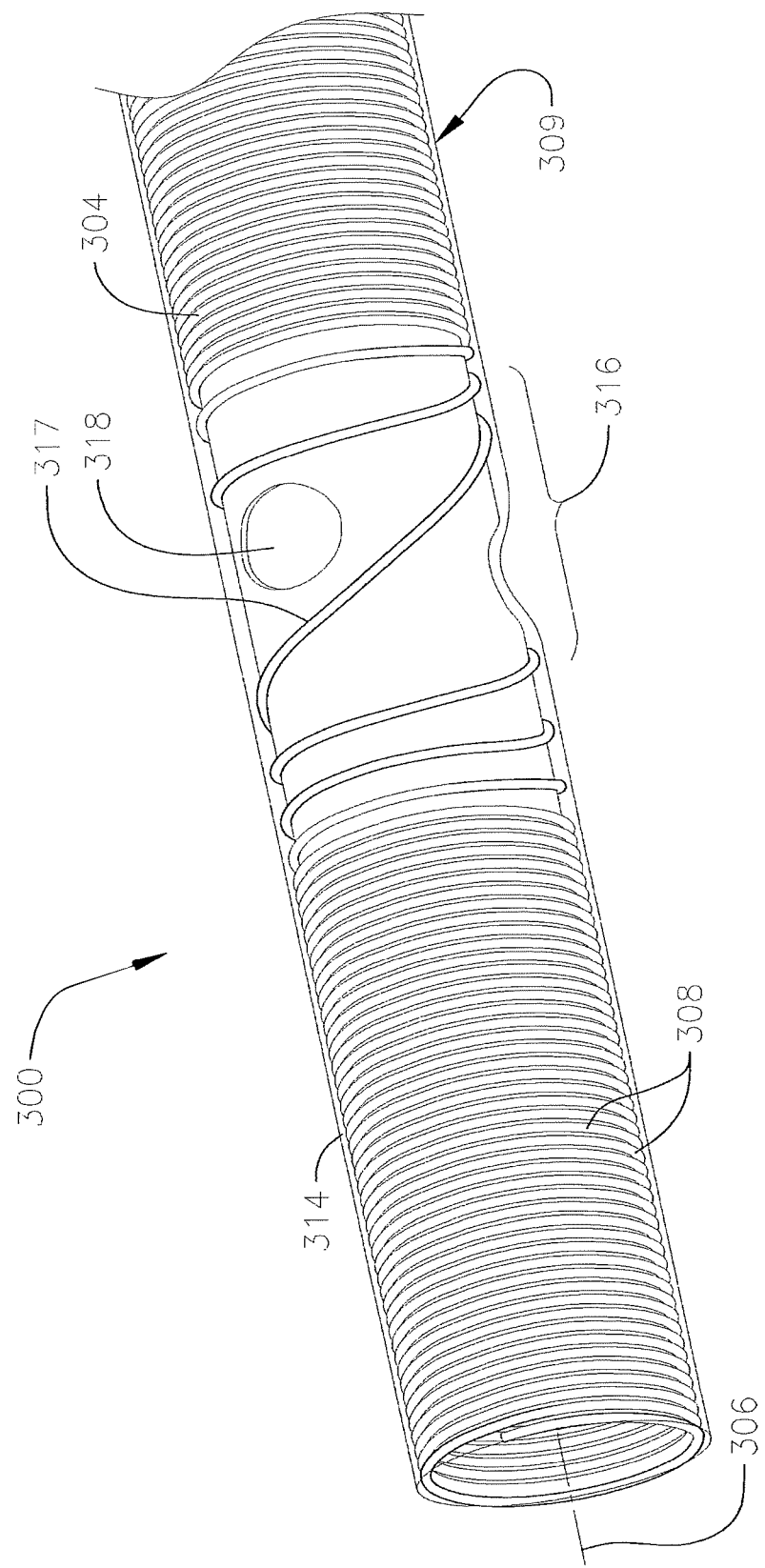
FIG. 9 is a perspective view of a portion of a wire body of another alternative spring cannula in which a porous region comprises an elongated coil and a coating having holes.
Figure 10:
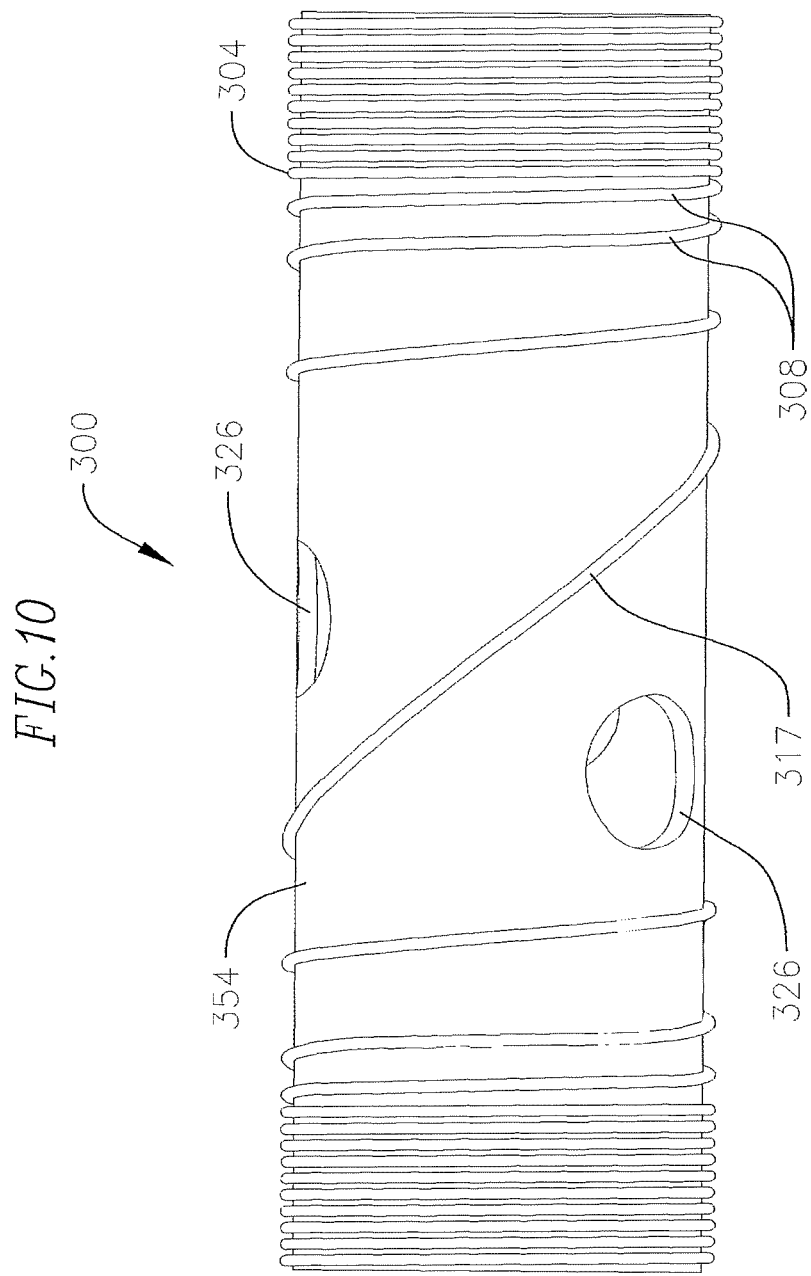
FIG. 10 is a side view of a portion of the spring cannula of FIG. 9 coiled onto a mandrel, with some of the coils spaced apart axially to provide space therebetween for formation of sidewall holes.

FIGS. 9 and 10 show a portion of a wire body 309 of another alternative spring cannula 300 in which a porous region 316 comprises a coil portion 317 that is stretched apart axially, and a coating 314 having holes 318.

The coiled spring 300 includes the axially stretched coil portion 317, which is wound at a smaller angle relative to a longitudinal axis 306 of the cannula 300 than the other adjacent coils such that it extends axially between the markings 326 so as to provide enough space between the coil portion and the adjacent coils to later form holes in the sidewall of the cannula without cutting the coils. In some embodiments, the coil portion 317 is elongated in an axial dimension relative to adjacent coils, such that a group of adjacent coils comprising the coil portion 317 covers an axial distance greater than an axial distance covered by a group of the same number of adjacent coils in other portions of the cannula 300. In some embodiments, the axial distance covered by the coil portion 317 can be at least as great as the axial length, or diameter, of a corresponding hole. In some embodiments, there can be two or more holes adjacent to the coil portion 317, such as one hole on either side of the coil. The two or more holes 318 placed adjacent to the coil portion can be axially and/or circumferentially offset from one another. In some embodiments, the coil portion 317 includes multiple coils, where the distance between the coils is sufficient to allow a hole to be punched between the coil portions.

In some embodiments, the wire 304 is a stainless steel wire. In some embodiments, the wire is coated with a polymeric coating, for example, with a thermoplastic polyurethane elastomer such as Pellethane®. After the coils 308 are wound, the wire can be heat-treated such that the polymeric coating melts to form a coating that encases the coils 308, and forms the cannula 300. Holes 318 can then be made in the coating 314 at locations commensurate with markings 326 on a mandrel 354, such that the holes 318 do not interrupt the coils 308.

As shown in FIG. 10, the generally cylindrical mandrel 354 has markings 326 that are commensurate with the locations of the holes 318 that will be formed in the resultant cannula 300. The markings can be holes in the mandrel, raised knobs, pegs, a template or guide markings on the surface of the mandrel, or any other indicator that shows the locations where the holes will eventually be in the cannula. A wire 304 is wound around the mandrel 354, to form coils 308. At least one coil portion 317 can be formed to prevent the coils from overlapping with the markings 304. In some embodiments, the mandrel is pre-coated with a thin coating, such as a urethane tubing, prior to winding the wire 304, and an overcoat 311 is applied after the wire 304 is wound. The mandrel is then heat and pressure treated to fuse the coatings together. However, the areas with the coil portion may have decreased adhesive and weak kink characteristics compared to adjacent tightly wound areas.

In another alternative embodiment, a mandrel around which the wire is wound can comprises pegs or projections on the radially outer surface of the mandrel. The pegs can have an outer diameter substantially equal to the inner diameter of the desired holes. As the wire is wound around the mandrel to form a plurality of coils, the wire can also be wound around the projections so as to define the hole locations and reinforce the perimeter of the holes. The wire may or may not overlap itself in such embodiments. In some embodiments, after winding, the projections can be removed from the mandrel and then the mandrel is removed from the resulting coiled wire, resulting in a wire wound substantially concentrically (except for any overlapping wire locations) about a central axis, with sidewall hole locations defined by the wire.

Figure 11:
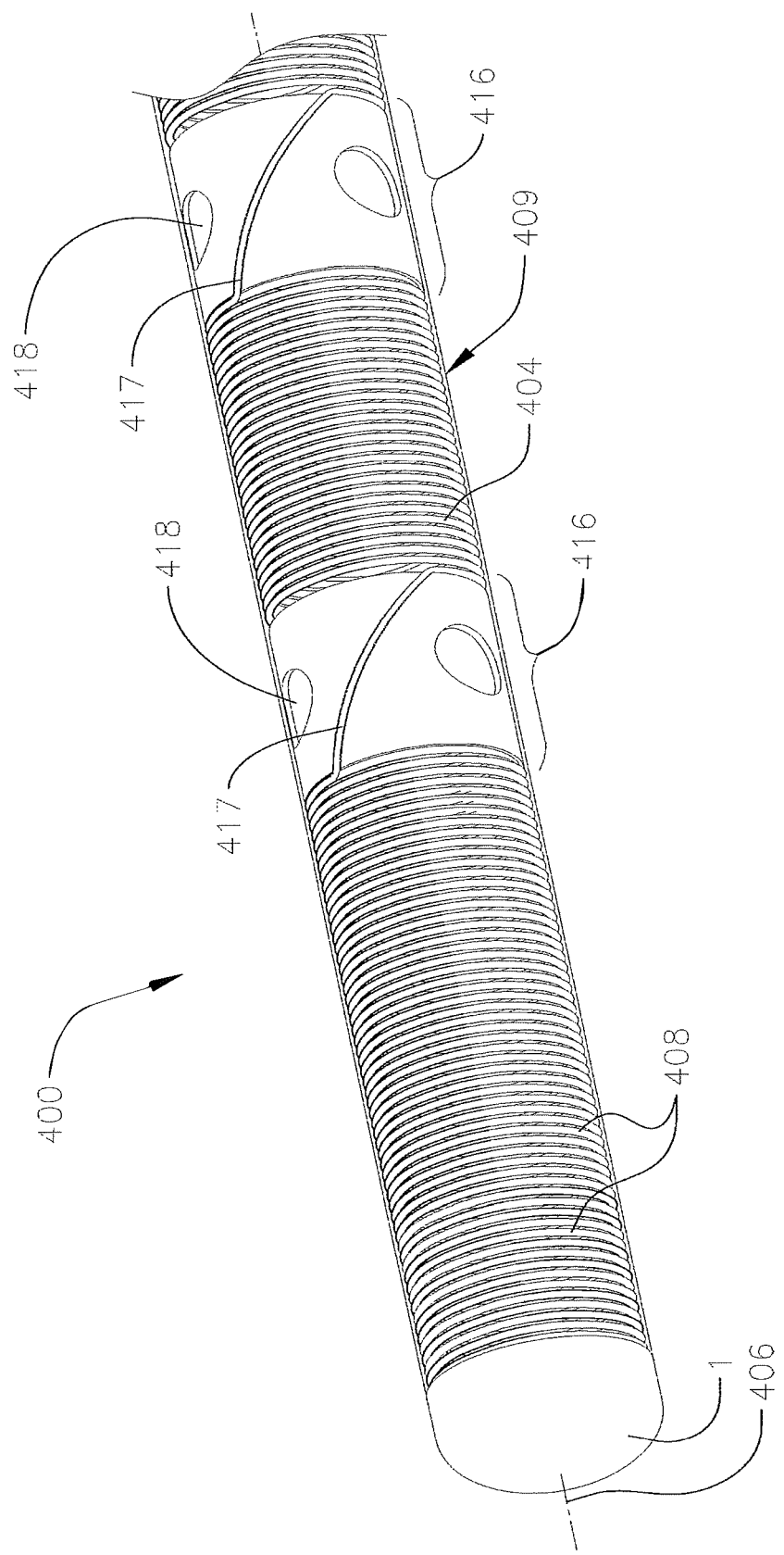
FIG. 11 is a perspective view of a distal portion of a spring cannula according to yet another embodiment in which the porous portions are transition sections.

FIG. 11 shows a distal portion of another spring cannula 400 in which the porous portions are transition sections 416.

The spring cannula 400 includes a wire body 409 having transition sections 416 inserted between adjacent coils 408 of the wire body 409. A wire 404 makes up the wire body 409 and is continuous through the transition sections 416 due to a coil portion 417 that extends at an angle across the transition section 416. The coil portion 417 is wound at a smaller angle relative to a longitudinal axis 406 of the cannula 400 than its adjacent coils, creating a wire body 409 with a variable pitch. The coil portion 417 allows the wire 404 of the spring cannula 400 to be continuous, without intervening cut ends by the transition sections 416, helping to reduce and prevent cannula breakage, to provide additional strength and to reduce the potential for process failures. In addition, the continuous wire 404 provides redundant wire support in the transition sections 416. Transition sections 416 and the adjacent coils of the wire 404 can be exposed to a localized heat and/or compression to fuse the transition sections and the adjacent coils together, further helping to improve the bond strength between each of the transition sections and the adjacent coils. The use of localized heating helps to reduce the amount of rework that may otherwise be required during manufacture. Further, the coil portion 417 provides additional surface area to increase bonding between the wire 404 and the transition sections 416.

Each transition section 416 is tubular in shape and includes one or more holes 418. In the illustrated embodiment, in each of the transition sections 416, three holes 418 are evenly spaced circumferentially and the holes 418 are axially aligned. However, the number of holes 418 in each transition section 416 can vary depending on the application. In some embodiments, the holes 418 are drainage holes to drain blood from in and around the right heart of a patient during a cardiopulmonary bypass.

The coil portion 417 extends axially between the holes 418. In some embodiments, the coil portion 417 is elongated in an axial dimension relative to adjacent coils such that a group of adjacent coils comprising the coil portion covers an axial distance greater than an axial distance covered by a group of the same number of adjacent coils in other parts of the cannula 400. In some embodiments, the axial distance covered by the coil portion 417 can be at least as great as the axial length, or diameter, of a corresponding hole. In some embodiments, there can be two or more holes adjacent to the coil portion 417, such as one hole on either side of the coil. The two or more holes 418 placed adjacent to the coil portion 417 can be axially and/or circumferentially offset from one another. In some embodiments, the coil portion 417 is at least the length of the transition section 416. In other embodiments, the coil portion 417 is shorter than the length of the transition section 416.

The transition sections 416 can be made of a thermoplastic polyurethane elastomer (TPU), similar to the TPU used to form the overcoat 11 shown in FIG. 1. For example, the transition sections 416 can be made of Tecothane™. In some embodiments, the transition sections 416 can have a diameter equal to or about 22 French. Tecothane™ can provide a smoother transition between the tightly coiled portions of the wire body surrounding the transition sections 416 than the previously used materials used in the solid-wall tubes of prior non-continuous spring cannulae, thus providing a superior feel to the spring cannula 400.

Figure 12A:
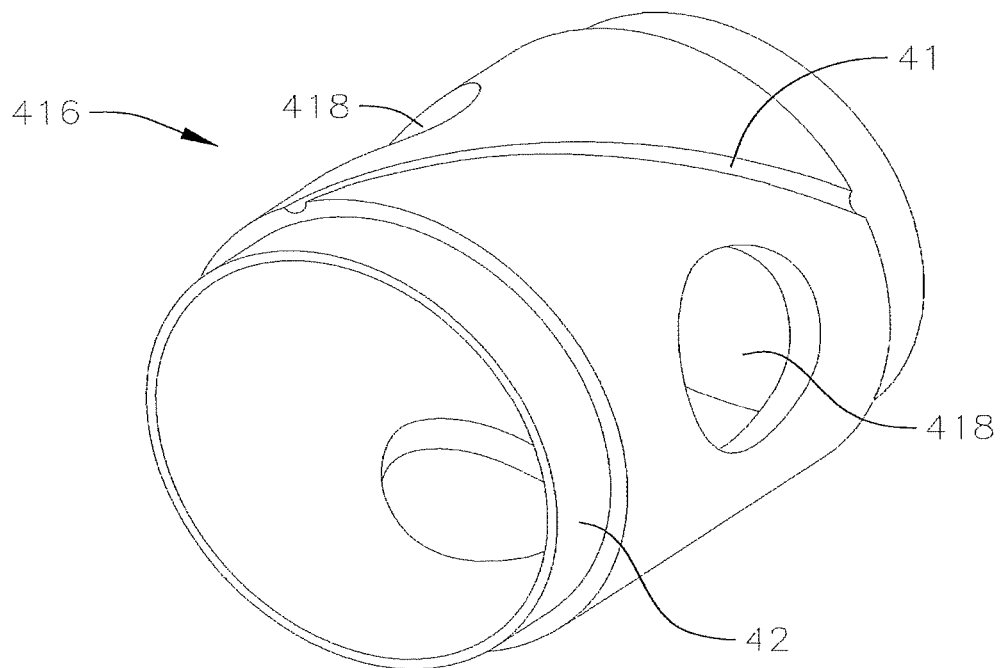
FIGS. 12A-12B are perspective views of transition sections that can be used with the spring cannula of FIG. 11.
Figure 12B:
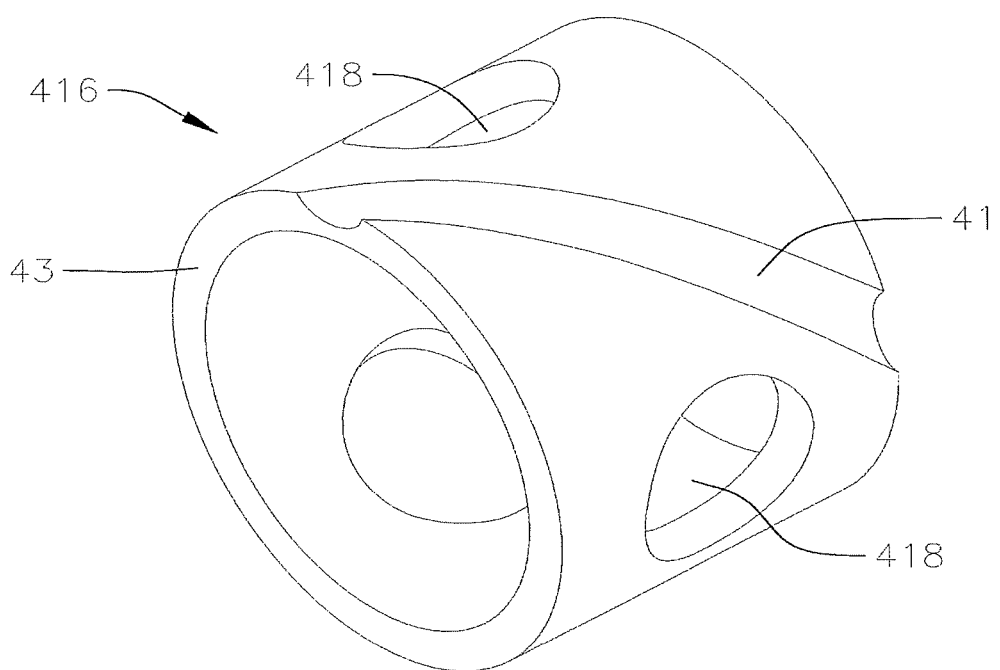

FIGS. 12A-12B show example transition sections 416, 416' that can be used with the spring cannula of FIG. 11.

FIG. 12A shows one transition section 416 that can be inserted between adjacent coils of the wire 404. The transition section 416 includes holes 418 as described above and a groove 41 into which the coil portion 417 can be inserted. The groove 41 provides a pathway for the coil portion 417 to stay in place and the groove 41 increases the surface area of contact between the coil portion 417 and the transition section 416 to allow for increased bonding between the coil portion 417 and the transition sections 416 when the transition section 416 and adjacent coils are heated or compressed as discussed above.

The transition section 416 further includes overlap joints 42 on both ends of the tubular body of the transition section 416. The overlap joints 42 have an outer diameter smaller than the central portion of the transition section 416. The difference between the outer diameter of the overlap joint 42 and the outer diameter of the central portion of the transition section 416 is such that the coils 408 of the wire 404 can wrap around the overlap joint 42 without protruding past the outer diameter of the central portion of the transition section 416 in an axial direction. In some embodiments, the outer diameter of the overlap joints 42 with coils 408 of the wire 404 wrapped around it is substantially equal to the outer diameter of the central portion of the transition section 416 to provide a continuous external diameter of the wire body 409. The overlap joints 42 increase the surface area between the transition section 416 and the adjacent coils of the wire 404. Thus, when the transition section 416 and the adjacent coils of the wire 404 are exposed to a localized heat or compression to fuse the adjacent coils and the transition section together, the overlap joints 42 further help to improve the bond strength between the transition section 416 and its adjacent coils. In addition, the coil portion 417 will fuse with the groove 41.

FIG. 12B shows another transition section 416' that can be inserted between adjacent coils of the wire 404. The transition section 416' includes holes 418 and a groove 41 into which the coil portion 417 can be inserted, as described above. The transition section 416' does not include overlap joints, but has side surfaces 43 which will face side surfaces of the adjacent coils when the transition section 416' is inserted between adjacent coils of the wire 404. When the transition section 416' and the adjacent coils of the wire 404 are exposed to a localized heat or compression to fuse the adjacent coils and the transition section together, the side surfaces 43 of the transition section 416' will fuse with the side surfaces of the adjacent coils. In addition, the coil portion 417 will fuse with the groove 41.

The angle of the groove 41 can vary in different embodiments. In the embodiments of FIGS. 12A-12B, the groove 41 is shown to have about a 45 degree angle with respect to central axes of the transition sections 416, 416', which are coaxial with the central axis 406 of the spring cannula 400. In other embodiments, the groove can be parallel with the central axis of the transition section, for example, to more easily facilitate punching the holes into the transition section.

The transition sections can be pre-cut to the desired size and to have the groove 41. For example, a tube of thermoplastic polyurethane elastomer, such as Tecothane™, can be positioned on a mandrel and a helical slot cut along the tubing, the angle of the helical slot correlating to the angle desired for the groove 41. The tubing can then be cut into multiple transition sections. If overlap joints are desired, the ends of the cut transition sections can be further cut to reduce their diameter.

There are various methods that can be employed to manufacture the spring cannula 400. The manufacturing process generally includes joining the transition section 416, 416' with the wire body 409 and fusing them together with heat and/or pressure to make a consistent and continuous section of wire body 409. The wire body 409 can them be attached to the tip 1 and the connector 3, and an overcoat 11 can be applied according to various suitable methods known in the art. Methods of manufacturing the wire body 409 according to various embodiments of the invention are discussed below.

FIGS. 13A-13D show a method of making the spring cannula 400 of FIG. 11.

As shown in FIG. 13A, the wire body 409 is provided that includes the continuous wire 404 formed into coils 408. The wire 404 has a coating 414. The coating can be a polymeric material, for example, a thermoplastic polyurethane elastomer such as Pellethane®, that is coated on the wire 404 before the wire 404 is wound to form the wire body 409. After winding, the coated wire is heat-treated such that the polymeric coating on each coil bonds or fuses with the coating on the adjacent coils and forms the substantially continuous, flexible coating 414 that encases the coils 408. The helical coil may not have an additional overcoat over the coating at this point.

Figure 13C:
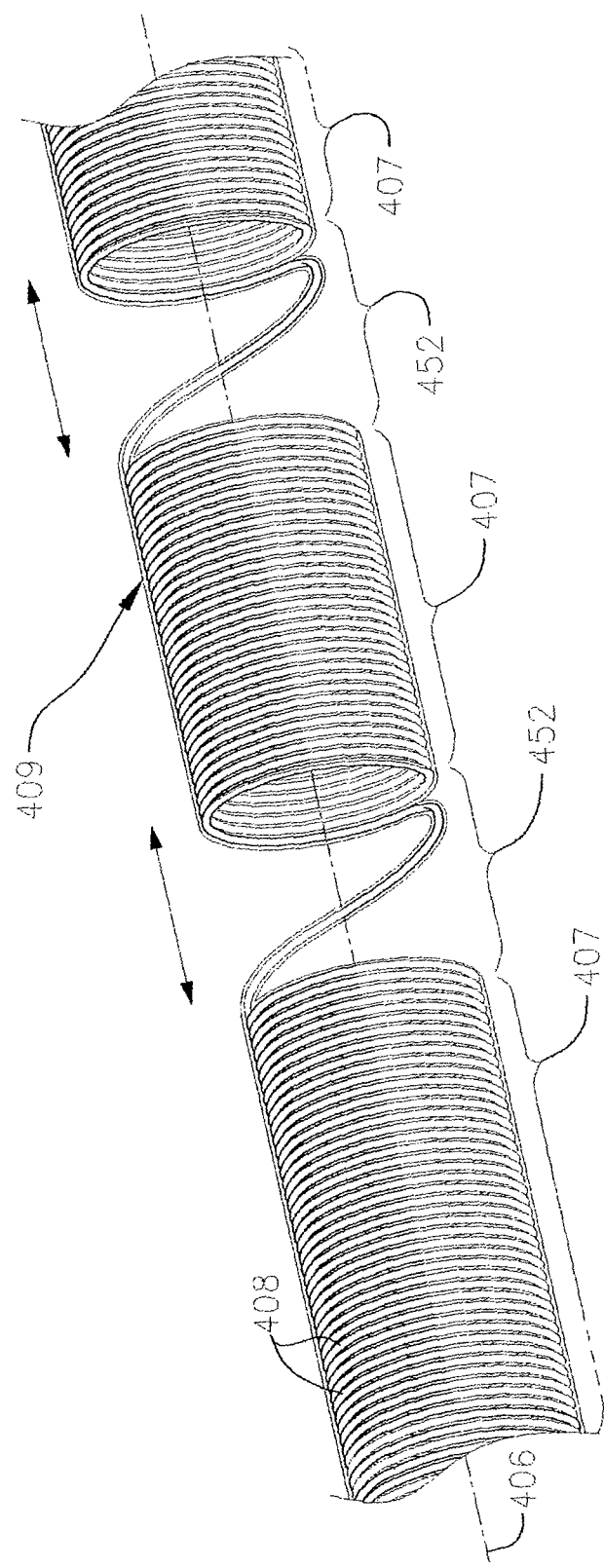

The wire body 409 is cut using, for example, a blade 450, as shown in FIG. 13B. The blade 450 cuts between two adjacent coils 408, but does not cut through the wire 404. The blade 450 merely cuts the coating 414 between two adjacent coils 408 to allow the adjacent coils to be separated from each other yet still attached to each other via the wire 404, as shown in FIG. 13C. The blade 450 or additional blades can be used to cut the wire body 409 in as many places as the number of transition sections 416 desired.

Once cut, the wire body 409 can be pulled apart along a direction of a central axis 406 of the wire body 409, creating wire reinforced regions 407. Between the regions 407, spaces 452 are formed. The regions 407 are pulled apart from one another until the spaces 452 are of sufficient width to allow insertion of the transition sections 416. The spaces are traversed by the wire 404 connecting the regions 407 on either side of the spaces 452.

Figure 13D:
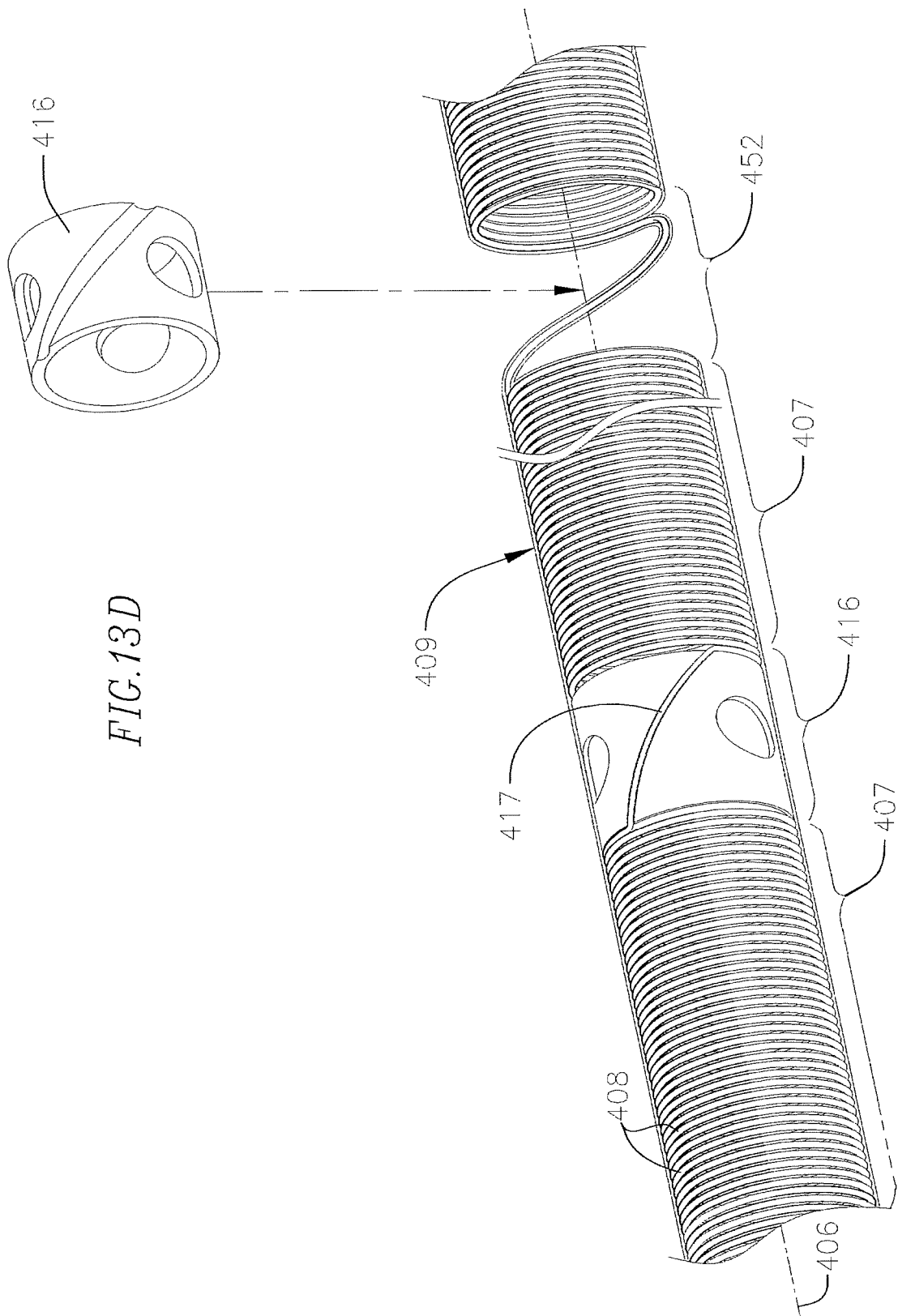

As shown in FIG. 13D, the transition sections 416 are inserted into the spaces 452. The transition sections 416 can be pre-cut to include the groove 41 for receiving the coil portion 417, can be pre-cut to include holes 418, and can also be pre-cut to include the overlap joints 42. To accommodate the overlap joints 42, the wire body 409 is pulled apart to provide sufficient space for the insertion of the transition sections 416 including the overlap joints 42, and then after insertion of the transition sections 416, regions 407 of the wire body 409 can be pushed together such that the coils 408 adjacent to the transition sections 416 overlap the overlap joints 42. In other embodiments, the transition sections can be pre-cut to include the side surfaces 43 instead of the overlap joints 42 and in such embodiments, pushing the regions 407 of the wire body 409 closer together for overlapping may be unnecessary. In alternative embodiments, the transition sections that are inserted may not be pre-cut to include either a groove, holes, or overlap joints, or more than one of these features.

Once the transition sections 416 are inserted, a mandrel can be inserted into the wire body 409 and the transition sections 416 to hold the transition sections 416 in position. In some embodiments, the transitions sections 416 can be cut entirely through. The mandrel can be inserted through the wire body 409 first in these embodiments, and the cut transition sections 416 can be placed over the mandrel corresponding to the coil portions 417 thereafter. The tip 1 can be added to an end of the mandrel after the wire body 409 and transition sections 416 have been positioned around the mandrel. The transition sections 416 and adjacent coils of the wire body 409 can then be wrapped with a fluoropolymer, such as a fluorinated ethylene propylene (FEP) film, and heat treated and pressure treated (e.g., such as via radial compression) to bond the transition sections 416 to the wire body 409. The tip 1 can also be bonded to the distal end of the wire body 409 at this time. In one embodiment, the wire body 409, the transition sections 416 and the tip 1, along with the PEP film, are heated using a hot box, such as a Beahm hot air bonder or similar heat treatment device. During the heat treatment, the cannula 400 can also be subjected to a constant rolling pressure or tension in order to imbed the coil portions 417 in the transition sections 416. In embodiments where the transition section does not include a groove, this heating process will also melt the transition section around the coil portion to surround the wire at the coil portion and fuse the wire with the transition section. After this bonding is complete, the heat and pressure can be removed and the FEP film can also be removed. At this point, various additional processing steps similar to how previous cannula have been manufactured can be performed, including punching holes 418 in the transition sections 416, adding an overcoat 14, and additional heat processing.

FIGS. 14A-14D show an alternative method of making the spring cannula 400 of FIG. 11.

As shown in FIG. 14A, transition sections 416 are loaded onto a winding mandrel 454 at predetermined distances from each other according to the distance desired in the final spring cannula 400. The tip 1 can also be pre-loaded onto the winding mandrel 454. The wire 404 is then tightly wound around the mandrel 545 until it reaches the first transition section 416, as shown in FIG. 14B. The wire 404 can be pre-coated with a polymeric material, for example, a thermoplastic polyurethane elastomer such as Pellethane®. The first transition section 416 is then rotated about the winding mandrel 454 until the groove 41 lines up with the next part of the wire 404 to be wound. The wire 404 is then wrapped over the transition section 416 in the groove 41, as shown in FIG. 14C. If a wire wrapping machine is used, the wire wrapping machine can be slowed to allow the transition sections 416 to be integrated, or a smart servo motor can be used to automate the process. The carriage or drive system can be programmed or adapted to form the variable pitch in the wire winding at the transition sections 416. The wire 404 continues to be wound about the mandrel 454 after the first transition section 416, and the same process used for the first transition section 416 is repeated when the wire 404 reaches the more proximal transition sections 416. After the last transition section 416 has been integrated, the wire 404 is wound about the mandrel 454 until the wire body 409 reaches a desired length. After winding is complete, the assembly can be placed into an oven, for example, an Accu-Heat oven, for curing and initial bonding. Then, localized zone heating and compression can be applied to the areas of the assembly corresponding to the transition sections 416, using, for example, the Beahm hot air bonder, similarly as discussed in the previously manufacturing method. Afterword, various suitable additional processing can be performed, including punching holes 418 in the transition sections 416, adding an overcoat 14 and additional heat processing.

In the embodiments shown thus far, the wire segment that traverses the transition sections is arranged at an angle. That is, the wire is wound around the cannula to a certain degree over the transition sections. In other embodiments, the wire traversing the transition sections can be substantially straight, for example, as shown in FIG. 15B, with little or no winding around the central axis of the cannula over the transition sections, for easier manufacturing. However, the partially wound embodiments may be more stable and desirable, due to an increased wire bonding length.

Figure 15A:
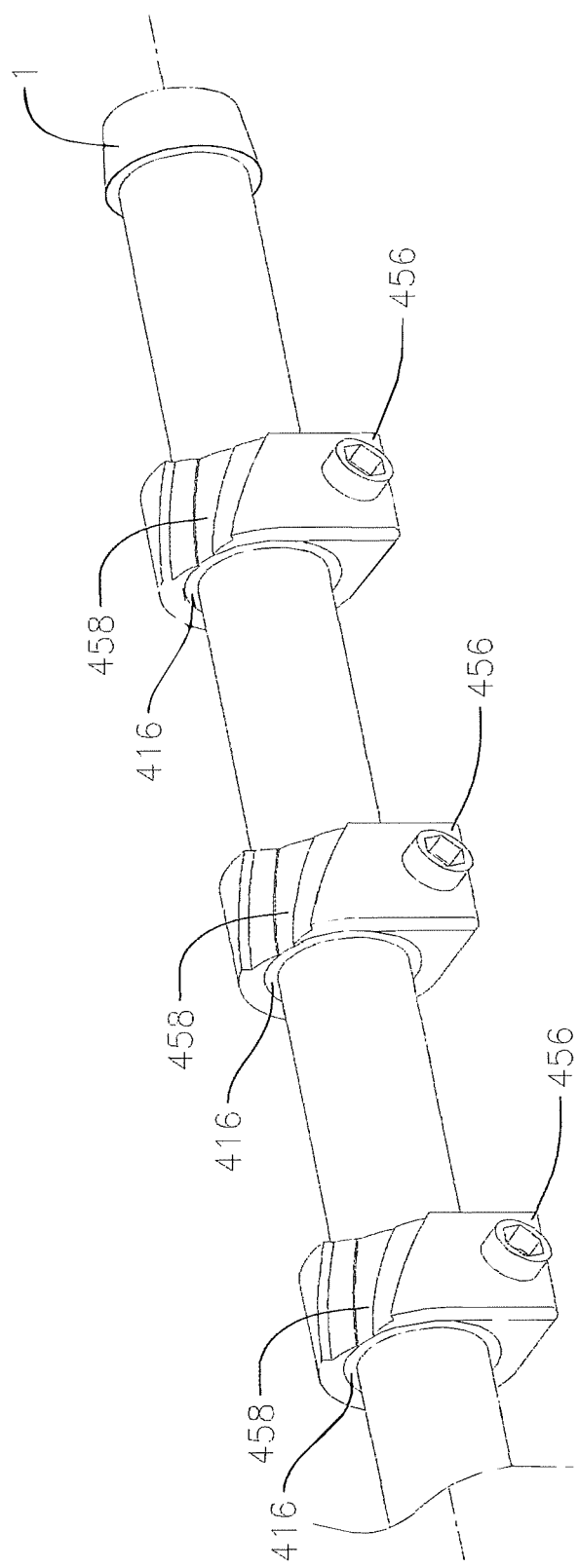
FIGS. 15A-15B shows a modification of the steps of FIGS. 14B-14C in which a clamp is included over the transition section.
Figure 15B:
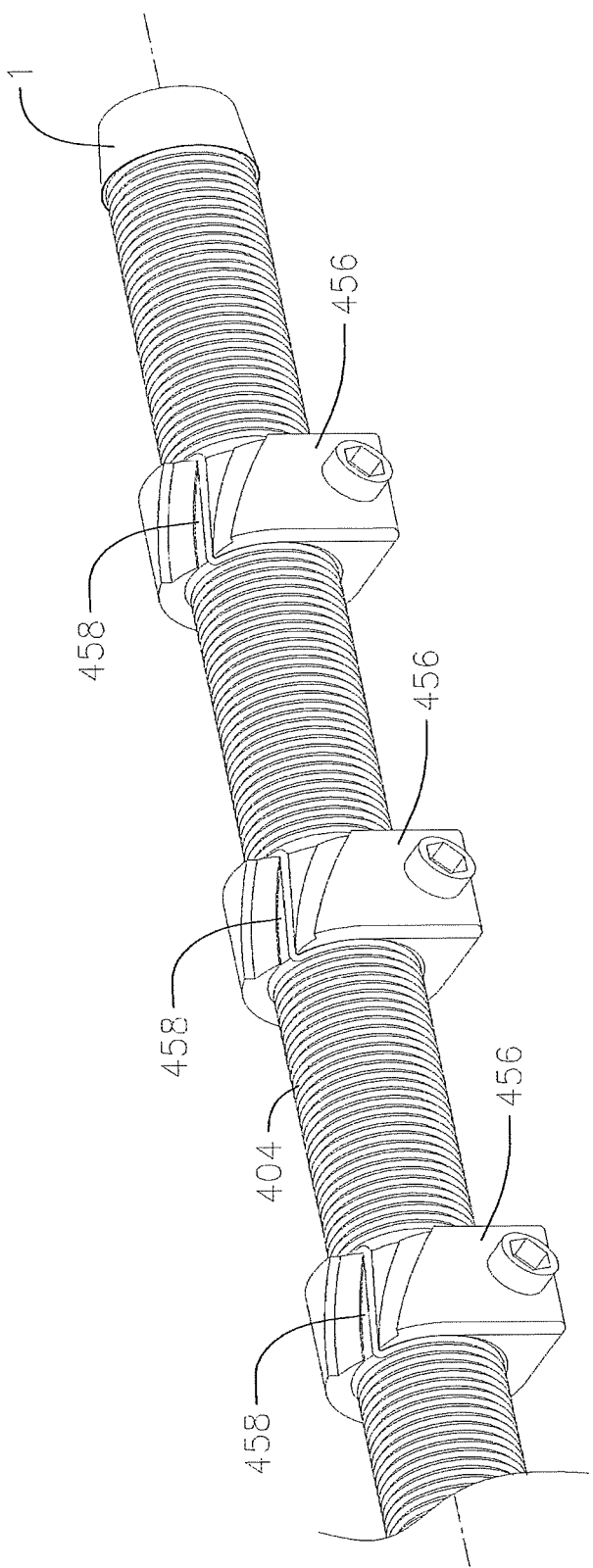

FIGS. 15A-15B shows a modification of the steps of FIGS. 14B-14C in which a clamp 456 is included over the transition section 416.

According to this method, the transition sections (and optionally the tip 1) are pre-loaded onto the winding mandrel 454 and the wire 404 is wound around the mandrel 454 until it reaches the first transition section 416, as discussed regarding FIG. 14A. In this method, however, each of the transition sections 416, includes a clamp 456 covering it, as shown in FIG. 15A. The clamp 456 has an opening 458 to guide the wire 404 as it crosses over the transition section 416. The opening 458 is aligned with the groove 41 of the transition section 416 in order to guide the wire 404 into the groove. However, in some embodiments, for example as shown in FIG. 15A, the transition section does not have a groove and the clamp guides the wire 404 across the transition section 416 without the aid of the groove.

The first transition section 416 can be rotated about the winding mandrel 454 until the opening 458 of the clamp 456 lines up with the next part of the wire 404 to be wound. The wire 404 is then wrapped over the transition section 416 with the aid of the clamp 456. A cyanoacrylate adhesive or thermal process can be applied to hold the wire 404 in place as it crosses over the transition section 416 in the opening 458 of the clamp 456. The wire 404 continues to be wound about the mandrel 454 after the first transition section 416 and the same process used for the first transition section 416 is repeated when the wire 404 reaches the additional transition sections, as shown in FIG. 15B. Afterwards, the clamps 456 can be removed. Further processing can be applied similarly as discussed with respect to the previous manufacturing methods.

In a further embodiment, only a single clamp can be used and can be moved from the first transition section to subsequent transition sections, to aid in the wire crossing over each of the transition sections.

Figure 16A:
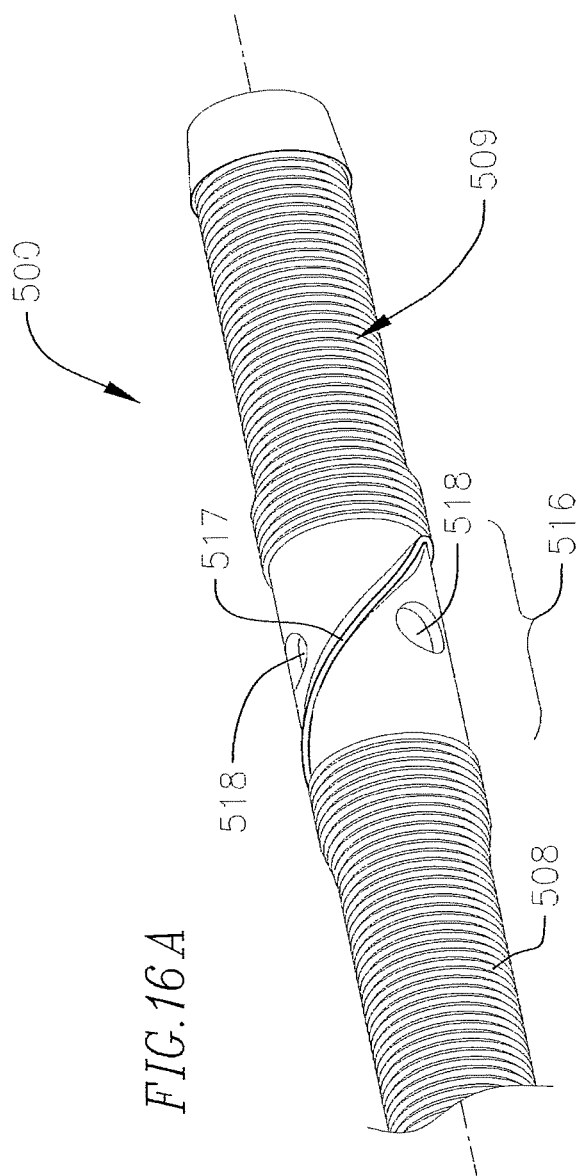
FIG. 16A is a perspective view of a distal portion of another spring cannula including a transition section having an extended body.
Figure 16B:
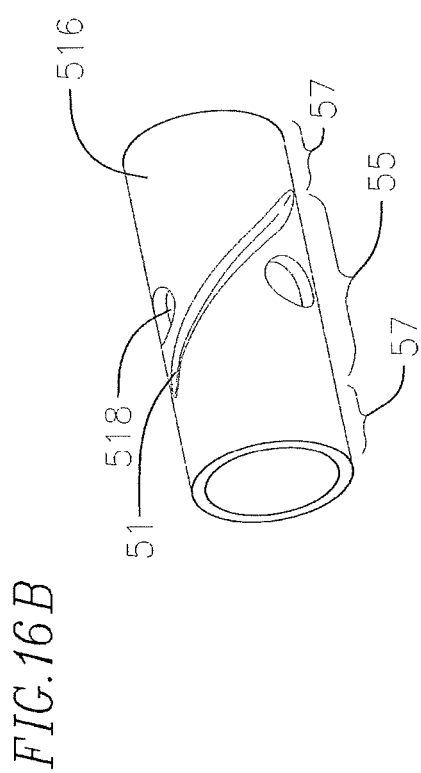
FIG. 16B is a perspective view of the extended body of the transition section of FIG. 16A.

FIG. 16A shows a distal portion of another spring cannula 500 including a transition section 516 having an extended body. FIG. 16B shows the extended body of the transition section of FIG. 16A.

Similar to the embodiment of FIG. 11, the spring cannula 500 includes a wire body 509 having transition sections 516 inserted between coils 508 of the wire body 509. However, the spring cannula 500 varies from the embodiment of FIG. 11 in that the transition section 516 has an elongated body including a central region 55, and two end regions 57, as shown in FIG. 16B. The central region 55 includes a groove 51 for receiving a coil portion 517 of the wire 504 and one or more holes 518. The groove 51 provides a pathway for an coil portion 517 of the wire body 509 to stay in place and the groove 51 increases the surface area of contact between the coil portion 517 and the transition section 516 to allow for increased bonding between the coil portion 517 and the transition sections 516 when the transition section 516 and adjacent coils are heated or compressed as discussed above.

The end regions 57 of the transition section 516 have the same outer diameter as the central region 55 and extend from the ends of the tubular body of the central region 55 to create a single uniform tubular body. The end regions 57 increase the surface area between the transition section 516 and the coils 508 of the wire 504 by providing a wide area for coils 508 of the wire to overlap the transition section 516, thus adding additional bond support. Thus, when the transition section 516 and the overlapping coils of the wire 504 are exposed to a localized heat or compression, the overlapping coils and the transition section are fused together, helping to improve the bond strength between the transition section 516 and the wire 504. This overlapping can provide greater flexibility and resistance to kinking than traditional cannulae.

The spring cannula 500 can be made similarly to the methods described above with respect to FIGS. 14A-15B. However, instead of stopping winding of the wire 504 around the mandrel when the transition section 516 is reached, the wire 504 continues to be wound on the first end region 57 of the transition section 516 until the wire 504 reaches and is aligned with the groove 51 at the central region 55. After the wire 504 is positioned in the groove 51, the wire 504 is wound on the second end region 57 of the transition section 516 until the end of the transition section 516, and then proceeds to be wound on the mandrel. Further winding and additional fabrication proceeds similarly as discussed with respect to the previous manufacturing methods. If a clamp is used according to the method of FIGS. 15A-15B, the clamp would only cover the central region 55 of the transition section 516.

The continuously wound cannulae 400 and 500 provide redundant systems to keep the cannulae together, while also reducing potential wire exposure due to the decrease of the number of ends of the wire 404, 504. The cannulae 400 and 500 have only two exposed wire ends, one at the tip and one at the connector; whereas prior cannulae had additional cut ends at each of the solid-walled sections of the cannulae having holes punched in them. The continuously wound cannulae 400 and 500 also allow for the wire to be continuously wound in a same direction, providing a consistent orientation of the variable pitch wire. The processes for making the cannulae 400, 500 also integrates multiple manufacturing steps together and decreases the number of heat processing steps needed to add the tip, overcoat, and transition sections.

For example, various known cannulae are manufactured by a multiple step manufacturing process that involves at least three separate oven heating steps. In contrast, in the spring cannulae 400, 500, the manufacturing steps are consolidated and the number of steps is reduced.

Figure 17:
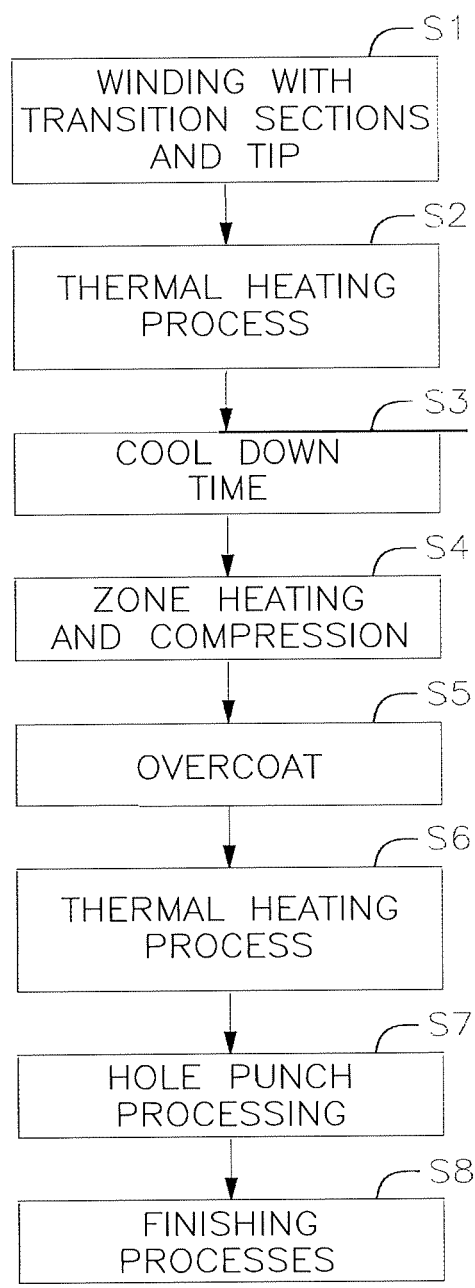
FIG. 17 is a flowchart of a method of manufacturing the spring cannulae of FIGS. 11 and 16A-16B.

In a first manufacturing process, shown in FIG. 17, the winding step (51) includes winding the wire and incorporating the transition sections and tip, as discussed in detail above. The wire body is then placed through thermal heat processing, for example, by being heat treated in an oven, such as an Accu-Heat Oven, while wrapped in FEP (S2). The wire body is then allowed to cool (S3) before being further subject to localized zone heating and compression (S4) to strengthen regions around the transition sections. An overcoat is then applied (S5) and the cannula is again placed through thermal heat processing to cure the overcoat (S6). Afterword, the transition sections are hole punched (S7) and additional finishing steps are performed (S8). As shown, only two oven heating steps are used in manufacturing methods according to embodiments of the invention.

Figure 18:
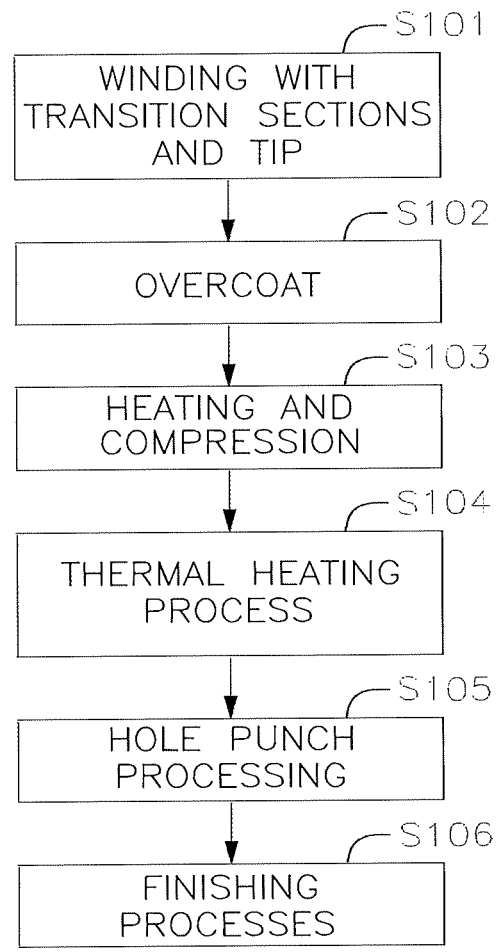
FIG. 18 is a flowchart of an alternative method of manufacturing the spring cannulae of FIGS. 11 and 16A-16B.

In another manufacturing process, shown in FIG. 18, the winding step (S101) includes winding the wire and incorporating the transition sections and tip, similarly as discussed in the previous manufacturing method. An overcoat is then applied (S102), and the wire body with the overcoat is then subjected to localized zone heating and compression (S103) to bond and/or strengthen the regions around the transition sections. The cannula is then placed through thermal heat processing, for example, by oven heating (S104). Afterword, the transition sections are hole punched (S105) and additional finishing steps are performed (S106). As shown, in this manufacturing process, only one oven heating step is used.

According to the embodiments of the invention, a cannula can be manufactured by winding a continuous wire, without fully separating or severing the wire. In addition, manufacturing methods can be used to reduce into a single winding step the previously separate steps of incorporating solid-walled sections into the cut wire and incorporating the tip. As a result, the separate oven heating steps needed for incorporating these portions is likewise reduced.

For purposes of this description, certain aspects, advantages, and novel features of the embodiments of this disclosure are described herein. The disclosed methods, apparatuses, and systems should not be construed as limiting in any way. Instead, the present disclosure is directed toward all novel and nonobvious features and aspects of the various disclosed embodiments, alone and in various combinations and sub-combinations with one another. The methods, apparatuses, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

In view of the many possible embodiments to which the principles of the disclosure may be applied, it should be recognized that the illustrated embodiments are only preferred examples and should not be taken as limiting the scope of the disclosure. Rather, the scope of the disclosure is defined by the following claims.

What is claimed is:

1. A cannula comprising:
a wire that is helically wound to form a plurality of coils, wherein the plurality of coils comprises at least one coil portion that is wound at a smaller angle relative to a central axis of the cannula than adjacent coils positioned at opposite ends of the at least one coil portion; and
an insert comprising a porous section defining at least one hole passing radially through the insert, wherein the insert is positionable between the adjacent coils and the at least one coil portion is positionable on the insert and is spaced apart from the at least one hole.

2. The cannula of claim 1, wherein the at least one hole does not interrupt any of the coils.

3. The cannula of claim 1, wherein the insert comprises a groove and the at least one coil portion is positioned in the groove.

4. The cannula of claim 1, wherein the at least one coil portion extends parallel to the central axis of the cannula.

5. The cannula of claim 1, wherein the porous section of the insert defines three holes.

6. The cannula of claim 5, wherein the three holes are spaced apart from one another equally in a circumferential direction around the porous section of the insert.

7. The cannula of claim 1, wherein the insert comprises a thermoplastic polyurethane elastomer.

8. A cannula comprising:
a wire that is helically wound to form a plurality of coils, wherein the plurality of coils comprises a first stretched coil portion that is wound at a smaller angle relative to a central axis of the cannula than adjacent coils positioned at opposite ends of the first stretched coil portion such that the first stretched coil portion is stretched axially relative to the adjacent coils; and
an insert comprising a first porous section defining at least one hole passing radially into the first porous section, wherein the first porous section is positioned along a length of the first stretched coil portion, with a portion of the wire defining the first stretched coil portion positioned on an exterior surface of the first porous section.

9. The cannula of claim 8, wherein the portion of the wire defining the first stretched coil portion does not obstruct the at least one hole passing radially into the first porous section.

10. The cannula of claim 8, wherein the plurality of coils comprises a second stretched coil portion that is wound at a smaller angle relative to the central axis of the cannula than adjacent coils positioned at opposite ends of the second stretched coil portion such that the second stretched coil portion is stretched axially relative to the adjacent coils.

11. The cannula of claim 10, wherein the insert comprises a second porous section defining at least one hole passing radially into the second porous section, wherein the second portion section is positioned along a length of the second stretched coil portion, with a portion of the wire defining the second stretched coil portion positioned on an exterior surface of the second porous section.

12. The cannula of claim 8, wherein the plurality of coils comprises a third stretched coil portion that is wound at a smaller angle relative to the central axis of the cannula than adjacent coils positioned at opposite ends of the second stretched coil portion such that the third stretched coil portion is stretched axially relative to the adjacent coils.

13. The cannula of claim 12, wherein the insert comprises a third porous section defining at least one hole passing radially into the third porous section, wherein the third portion section is positioned along a length of the third stretched coil portion, with a portion of the wire defining the third stretched coil portion positioned on an external surface of the third porous section.

14. A cannula comprising:
   a wire that is helically wound to form a plurality of coils, wherein the plurality of coils comprises at least two compressed coil portions wherein the coils are coiled such that adjacent coils are touching each other, the plurality of coils comprises at least one stretched coil portion that is wound at a smaller angle relative to a central axis of the cannula than adjacent coils positioned at opposite ends of the at least one coil portion; and
   an insert comprising a porous section defining at least one hole passing radially through the insert, wherein the insert is positioned between the two compressed coil portions and the at least one stretched coil portion is positioned on the insert and is spaced apart from the at least one hole.

15. The cannula of claim 14, wherein the at least one hole does not interrupt any of the coils.

16. The cannula of claim 14, wherein the insert comprises an external surface with a groove in the external surface, wherein the at least one coil portion is positioned in the groove.

17. The cannula of claim 14, wherein the at least one stretched coil portion extends parallel to the central axis of the cannula.

18. The cannula of claim 14, wherein the porous section of the insert defines three holes.

19. The cannula of claim 18, wherein the three holes are spaced apart from one another equally in a circumferential direction around the porous section of the insert.

20. The cannula of claim 14, wherein the insert comprises a thermoplastic polyurethane elastomer.

* * * * *